(12) United States Patent
von Borstel et al.

(10) Patent No.: US 7,776,838 B1
(45) Date of Patent: Aug. 17, 2010

(54) TREATMENT OF CHEMOTHERAPEUTIC AGENT AND ANTIVIRAL AGENT TOXICITY WITH ACYLATED PYRIMIDINE NUCLEOSIDES

(75) Inventors: Reid W. von Borstel, Potomac, MD (US); Michael K. Bamat, Potomac, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 08/460,186

(22) Filed: Jun. 2, 1995

Related U.S. Application Data

(60) Division of application No. 08/176,485, filed on Dec. 30, 1993, now Pat. No. 5,736,531, which is a continuation-in-part of application No. 08/061,381, filed on May 14, 1993, now abandoned, which is a continuation-in-part of application No. 07/903,107, filed on Jun. 25, 1992, now abandoned, which is a continuation-in-part of application No. 07/724,340, filed on Jul. 5, 1991, now abandoned, which is a continuation-in-part of application No. 07/438,493, filed on Jun. 26, 1990, now abandoned, which is a continuation-in-part of application No. 07/115,929, filed on Oct. 28, 1987, now abandoned, said application No. 07/724,340 is a continuation-in-part of application No. 07/487,984, filed on Feb. 5, 1990, now abandoned, which is a continuation-in-part of application No. 07/115,923, filed on Oct. 28, 1987, now abandoned.

(51) Int. Cl.
*A61K 31/7068* (2006.01)
*A61K 31/7072* (2006.01)
*C07H 19/067* (2006.01)
*C07H 19/12* (2006.01)

(52) U.S. Cl. .................. 514/49; 514/50; 536/28.5; 536/28.51; 536/28.53

(58) Field of Classification Search .......... 514/49, 514/50
See application file for complete search history.

(56) References Cited

U.S. PATENT DOCUMENTS

| | | | |
|---|---|---|---|
| 3,161,565 A | | 12/1964 | Vigneron |
| 4,017,606 A | * | 4/1977 | Hanze et al. ............ 514/49 |
| 4,757,139 A | * | 7/1988 | Kawaguchi et al. ...... 536/28.53 |
| 4,868,162 A | * | 9/1989 | Kawaguchi et al. ........ 514/50 |
| 4,874,602 A | | 10/1989 | Calabresi et al. |
| 4,950,466 A | | 8/1990 | Calabresi et al. |
| 5,077,280 A | | 12/1991 | Sommadossi et al. |
| 5,141,943 A | | 8/1992 | Naguib et al. |
| 5,246,708 A | | 9/1993 | von Borstel et al. |
| 5,470,838 A | * | 11/1995 | von Borstel et al. ........ 514/50 |
| 5,583,117 A | * | 12/1996 | von Borstel et al. ........ 514/50 |
| 5,691,320 A | * | 11/1997 | von Borstel et al. ........ 514/50 |
| 5,736,531 A | * | 4/1998 | von Borstel et al. ........ 514/50 |
| 5,770,582 A | * | 6/1998 | von Borstel et al. ........ 514/45 |
| 5,968,914 A | * | 10/1999 | von Borstel et al. ........ 514/50 |
| 6,020,320 A | * | 2/2000 | von Borstel et al. ........ 514/46 |
| 6,020,322 A | * | 2/2000 | von Borstel et al. ........ 514/50 |
| 6,054,441 A | * | 4/2000 | von Borstel et al. ........ 514/45 |
| 6,060,459 A | * | 5/2000 | von Borstel et al. ........ 514/45 |
| 6,103,701 A | * | 8/2000 | von Borstel et al. ........ 514/46 |
| 6,232,298 B1 | * | 5/2001 | von Borstel et al. ........ 514/49 |
| 6,255,290 B1 | * | 7/2001 | von Borstel et al. ........ 514/45 |
| 6,258,795 B1 | * | 7/2001 | von Borstel et al. ........ 514/49 |
| 6,274,563 B1 | * | 8/2001 | von Borstel et al. ........ 514/50 |
| 6,297,222 B1 | * | 10/2001 | von Borstel et al. ........ 514/45 |
| 6,306,834 B1 | * | 10/2001 | von Borstel et al. ........ 514/45 |
| 6,316,426 B1 | * | 11/2001 | von Borstel et al. ........ 514/50 |
| 6,329,350 B1 | * | 12/2001 | von Borstel et al. ........ 514/50 |
| 6,344,447 B2 | * | 2/2002 | von Borstel et al. ........ 514/49 |
| 6,348,451 B1 | * | 2/2002 | von Borstel et al. ........ 514/49 |
| 6,403,565 B1 | * | 6/2002 | von Borstel et al. ........ 514/45 |
| 6,417,170 B2 | * | 7/2002 | von Borstel et al. ........ 514/45 |
| 6,465,440 B2 | * | 10/2002 | von Borstel et al. ........ 514/45 |
| 6,472,378 B2 | * | 10/2002 | von Borstel ............. 514/50 |
| 6,743,782 B1 | * | 6/2004 | Von Borstel et al. ........ 514/46 |
| 6,992,072 B2 | * | 1/2006 | Walker ................. 514/49 |

FOREIGN PATENT DOCUMENTS

| | | |
|---|---|---|
| EP | 0 056 265 | 7/1982 |
| GB | 1 297 398 | 11/1972 |
| GB | 1 473 148 | 5/1977 |
| JP | 60-174797 | 2/1984 |
| JP | S60-126221 | * 7/1985 |

(Continued)

OTHER PUBLICATIONS

Chu et al., "Potentiation of 5-Fluoro-2'-deoxyuridine Antineoplastic Activity by the Uridine Phosphorylase Inhibitors Benzylacyclouridine and Benzyloxybenzylacyclouridine" Cancer Research (1984) vol. 44, pp. 1852-1856.*

(Continued)

*Primary Examiner*—Eric S Olson
(74) *Attorney, Agent, or Firm*—Lewis J. Kreisler

(57) ABSTRACT

The subject invention discloses compounds, compositions and methods for treatment and prevention of toxicity due to chemotherapeutic agents and antiviral agents. Disclosed are acylated derivatives of non-methylated pyrimidine nucleosides. These compounds are capable of attenuating damage to the hematopoietic system in animals receiving antiviral or antineoplastic chemotherapy.

11 Claims, No Drawings

FOREIGN PATENT DOCUMENTS

| | | |
|---|---|---|
| JP | 3-135918 A | 6/1991 |
| JP | 3-169815 | 7/1991 |
| WO | WO 85/00608 | 2/1985 |
| WO | WO85/00608 * | 2/1985 |
| WO | WO 89/03837 | 5/1989 |
| WO | WO 89/03838 | 5/1989 |
| WO | WO 89/09603 | 10/1989 |
| WO | WO 90/08550 | 8/1990 |
| WO | WO 90/09163 | 8/1990 |
| WO | WO 91/16315 | 10/1991 |

OTHER PUBLICATIONS

2006 Chemical Abstracts Catalog, published 2006 by Chemical Abstracts Service, p. 52.*

Merriam-Webster's Collegiate Dictionary, Tenth Edition, published 1998 by Merriam-Webster, Incorporated, p. 924.*

Silverman, The Organic Chemistry of Drug Design and Drug Action, published 1992 by Academic Press, pp. 352-397.*

The Merck Manual of Diagnosis and Therapy, Seventeenth Edition, pubished 1999 by Merck Research Laboratories, pp. 990, 994, 995, 1132, 1133, and 1332.*

Davidson et al., "'Platinum-Pyrimidine Blues' and Related Complexes: A New Class of Potent Antitumor Agents" Cancer Chemotherapy Reports (1975) vol. 59 No. 2 pt. 1 pp. 287-300.*

Kralovanszky et al., Cancer Chemotherapy and Pharmacology, 1993, vol. 32: 243-248, "Biochemical consequences of 5-fluorouracil gastrointestinal toxicity in rats; effect of high dose uridine".

Calabresi et al., Blood, 1990, vol. 76, No. 11: 2210-2215, "Benzylacyclouridine Reverses Azidothymidine-Induced Marrow Suppression Without Impairment of Anti-Human Immunodeficiency Virus Activity".

Davis et al., Biochemical Pharmacology 1993, vol. 45 No. 1: 173-181, "Species Dependent Differences in the Biochemical Effects and Metabolism of 5-Benzylacyclouridine".

Kelsen et al. "Phase I trial of PN401, an oral prodrug of uridine, to prevent toxicity from fluorouracil in patients with advanced cancer" J. Clin. Oncol. 15:1511-1517 (1997).

Peters et al. "In vitro biochemical and in vivo biologicals studies of the uridine 'rescue' of 5-fluorouracil" Brit. J. Cancer 57:259-265 (1988).

D.S. Martin et al, Cancer Res., 42, 3964-3970, 1982, "High-Dose 5-Fluorouracil with Delayed Uridine 'Rescue' in Mice."

D.S. Martin et al., Cancer Res., 43, 4653, 1983, "Improved Therapeutic Index with Sequential N-Phosphonacetyl-L-asparate plus High-Dose Methotrexate plus High-Dose 5-Fluorouracil and Appropriate Rescue."

Proceedings of AACR, 28, 195, Mar. 1987—No. 775—"Phase I Clinical and Pharmacokinetics Study of Orally Administered Uridine."

C.J. van Groeningen et al, Cancer Treatment Reports, vol. 70, No. 6, 745, Jun. 1986, "Clinical and Pharmacokinetic Studies of Prolonged Administration of High-Dose Uridine Intended for Rescue from 5-FU Toxicity."

N.I. Belyanchikova et al, Byulleten 'Eksperimental' noi Biologii i Meditsiny, vol. 91, No. 1, p. 67-69, "Particular Features of Hematopoiesis in Mice Protected by Deoxycytidine Against the Lethal Effect of Cytosar.", (1981).

K. Bhalla et al, Blood, vol. 70, No. 2, Aug. 1987, pp. 568-571, "Deoxycytidine Preferentially Protects Normal Versus Leukemic Myeloid Progenitor Cells from Cytosine Arabinoside-Mediated Cytotoxicity."

S. Grant et al, Leukemia Research, M.S. 045, Pergamon Journals Ltd., "Interaction of Deoxycytidine and Deoxycytidine Analogs in Normal and Leukemic Human Myeloid Progenitor Cells.", (1986) vol. 10 No. 9 pp. 1139-1146.

K. Bhalla et al, Leukemia, vol. 2 (10) 709-10, 1988, "Phase I Clinical and Pharmacologic Study of Deoxycytidine."

J. Sommadossi et al, Timicrobial Agents and Chemotherapy, vol. 32, No. 7, p. 997-1001, Jul. 1988, "Uridine Reverses the Tosicity of 3'-Azido-3'-Deoxythymidine in Normal Human Granulocyte-Macrophage Progenitor Cells In Vitro without Impairment of jAntiretroviral Activity."

A. Falcone et al, Blood, vol. 76, No. 11, pp. 2216-2221, (Dec. 1, 1990), "Differential Effecto f Benzylacyclouridine on the Toxic and Therapeutic Effects of Azidothymidine in Mice."

K. Bhalla et al, Blood, vol. 74, No. 6, pp. 1923-1928 (Nov. 1, 1989), "2'-Deoxycytidine Protects Normal Human Bone Marrow Progenitor Cells In Vitro Against the Cytotoxicity of 3'-Azido-3'-Deoxythymidine with Preservation of Antiretroviral Activity."

Z. M. Gomez et al, Antimicrobial Agents and Chemotherapy, vol. 34, No. 7, p. 1371-1375, Jul. 1990, "Antimalarial Activity of a Combination of 5-Fluoroorotate and Uridine in Mice."

M. Iigo et al, Biochemical Pharmacology, vol. 39, No. 7, 1247 (1990), "Differential Effects of 2,2'-Anhydro-5-Ethyluridine, A Uridine Phosphorylase Inhibitor, on the Antitumor Activity of 5-Fluorouridine and 5-Fluoro-2'-Deoxyuridine."

P. Calabresi et al, Blood, vol. 76, No. 11, pp. 2210-2215 (Dec. 1990), "Benzylacyclouridine Reverses Azidothymidine-Induce Marrow Suppression Without Impairment of Anti-Human Immunodeficiency Virus Activity."

W.D. Ensminger et al, Biochemical Pharmacology, vol. 28, p. 1541-1545 (1979), "Thymidine 5'-O-Pivaloate, A Prodrug Derivative of Thymidine with Potential Applications in High-Dose Methotrexate Therapy."

Martin et al, Journal of Pharmaceutical Sciences, vol. 76, No. 2, pp. 180-183, issued Feb. 1987, "Synthesis and Antiviral Activity of Various Esters of 9-[(1,3-Dihydroxy-2-propoxy)methyl]guanine."

Casida et al, Biochemical Pharmacology, vol. 15, pp. 627-644, Issued 1966, "3',5'-Diesters of 5-Fluoro-2'-Deoxyuridine and Thymidine Hydrolysis by Esterases in Human, Mouse, and Insect Tissue."

Losse et al, Chemical Abstracts, vol. 118, Issued 1993, "A convenient pathway to 2'-(tert-butyloxycarbonyl)-ribonucleosides," p. 884, col. 1, abstr. No. 60026c, J. Prakt Chem./Chem.-Ztg., 334(6), 531-532.

Translation of Office Action mailed Jun. 1, 2004 in counterpart Japanese Patent Application No. 510442/94.

Bamat, M.K., et al; "Acylated Uridine and Cytidine and Uses Thereof"; (1989); Patent No. WO/8903837; (Abstract not Available).

Derwent Abstract No. 91-212578 of Japanese Publication JO 3135918 (Ajinomoto), Published 1991.

Kralovansky, et al., Cancer Chemother Pharmacol (1993) 32: 243-248.

* cited by examiner

TREATMENT OF CHEMOTHERAPEUTIC AGENT AND ANTIVIRAL AGENT TOXICITY WITH ACYLATED PYRIMIDINE NUCLEOSIDES

This is a Divisional of application Ser. No. 08/176,485, filed Dec. 30, 1993 now U.S. Pat. No. 5,736,531, which is a CIP of Ser. No. 08/061,381 filed May 14, 1993 now abandoned, which is a CIP of Ser. No. 07/903,107 filed Jun. 25, 1992 now abandoned, which is a CIP of Ser. No. 07/724,340 filed Jul. 5, 1991 (abandoned), which is a CIP of Ser. No. 07/438,493 filed Jun. 26, 1990 (abandoned), which is a CIP of Ser. No. 07/115,929 filed Oct. 28, 1987 (abandoned), and Ser. No. 07/724,340 Jul. 5, 1991 in turn is a CIP of Ser. No. 07/487,984 filed Feb. 5, 1990 (abandoned), which is a CIP of Ser. No. 07/115,923 filed Oct. 28, 1987 (abandoned). All of these applications are hereby incorporated by reference.

FIELD OF THE INVENTION

This invention relates generally to treatment of chemotherapeutic agent and antiviral agent toxicity with acylated derivatives of non-methylated pyrimidine nucleosides. These compounds are capable of attenuating damage to the hematopoietic system in animals receiving antiviral or antineoplastic chemotherapy. This invention also relates to protection of other tissues affected by antiviral or antineoplastic chemotherapy, including the gastrointestinal epithelium.

BACKGROUND OF THE INVENTION

A major complication of cancer chemotherapy and of antiviral chemotherapy is damage to bone marrow cells or suppression of their function. Specifically, chemotherapy damages or destroys hematopoietic precursor cells, primarily found in the bone marrow and spleen, impairing the production of new blood cells (granulocytes, lymphocytes, erythrocytes, monocytes, platelets, etc.). Treatment of cancer patients with 5-fluorouracil, for example, reduces the number of leukocytes (lymphocytes and/or granulocytes), and can result in enhanced susceptibility of the patients to infection. Many cancer patients die of infection or other consequences of hematopoietic failure subsequent to chemotherapy. Chemotherapeutic agents can also result in subnormal formation of platelets which produces a propensity toward hemorrhage. Inhibition of erythrocyte production can result in anemia. The risk of damage to the hematopoietic system or other important tissues can prevent utilization of doses of chemotherapy agents high enough to provide good antitumor or antiviral efficacy.

Many antineoplastic or antiviral chemotherapy agents act by inhibiting nucleotide biosynthesis, metabolism, or function, or are in fact nucleoside analogs that substitute for the normal nucleosides in nucleic acids, producing defective RNA or DNA.

5-Fluorouracil is a clinically important cytoreductive antineoplastic chemotherapy agent that acts in part through incorporation into RNA, producing defective RNA; inhibition of thymidylate synthetase by fluorodeoxyuridine monophosphate may also contribute to the cytotoxicity of 5-FU. The clinical utility of 5-FU is limited by its toxicity (especially to bone marrow). Specifically, its clinical utility is limited by a low therapeutic ratio (the ratio of toxic dose to effective dose; a high therapeutic ratio implies that a drug has efficacy with little toxicity).

5-FU and many other chemotherapy agents also affect other tissues, especially gastrointestinal mucosa, producing mucositis, diarrhea and ulceration. Stomatitis (ulceration of mucosa in the mouth), is particularly troublesome to patients, making eating and swallowing painful.

D. S. Martin et al. (*Cancer Res.* 42:3964-70 [1982]) reported that a toxic dose of 5-FU (with strong anti-tumor activity) could be safely administered to mice if followed by administration of a high dose of uridine beginning several hours later. This "rescue" strategy has been shown to increase the therapeutic index of 5-FU in animal tumor models, allowing administration of the high, toxic doses of 5-FU that are necessary for causing tumor regression or preventing tumor growth while preferentially protecting normal tissues (especially important is bone marrow) by subsequent administration of uridine (D. S. Martin et al., *Cancer Res.* 43:4653-61 [1983]).

Clinical-trials involving the administration of uridine have been complicated due to the biological properties of uridine itself. Uridine is poorly absorbed after oral administration; diarrhea is dose limiting in humans (van Groeningen et al., Proceedings of the AACR 28:195 [1987]). Consequently, parenteral administration of uridine is necessary for clinically significant reversal of 5-FU toxicity, which requires use of a central venous catheter, since phlebitis has been a problem in early clinical trials when uridine was administered via a small intravenous catheter (van Groeningen et al. *Cancer Treat Rep.* 70:745-50 [1986]). Prolonged infusion via central venous catheters requires hospitalization of the patients. Further, there is considerable discomfort and inconvenience to the patients.

Orally-active prodrugs of 5FU have been developed which are enzymatically or spontaneously converted to 5FU, generally after absorption from the intestine into the bloodstream. This permits self-administration by patients, without the discomfort of intravenous administration. Moreover, in some chemotherapy regimens, sustained exposure, e.g. a constant intravenous infusion for several days or weeks, of tumors to 5FU is attempted. Oral administration of 5FU prodrugs can in principle provide such sustained availability of 5FU to tumors.

5-Fluoro-1-(tetrahydro-2-furfuryl)uracil (FT) is an orally active prodrug of 5-fluorouracil. It is enzymatically converted to 5-fluorouracil primarily in the liver. The liver, however, has relatively high levels of the enzyme dihydropyrimidine dehydrogenase, which degrades 5FU, producing metabolites which are not useful in cancer chemotherapy and which furthermore contribute to 5-FU toxicity.

The cytotoxicity of 5FU, the active metabolite of FT, is believed to be a result of its incorporation into nucleotide pools, where certain anabolites exert toxic effects, e.g. 5-fluorodeoxyuridine monophosphate inhibits thymidylate synthetase, thus depriving cells of thymidine for DNA synthesis, and 5-fluorouridine triphosphate incorporation into RNA impairs its normal functions in translation of genetic information.

In order to inhibit the catabolism of 5FU derived from FT, other compounds have been administered with the FT. In particular, the pyrimidine uracil inhibits the catabolism of 5FU without inhibiting its cytotoxicity. The most widely used clinical formulation of FT contains uracil in a 1:4 molar ratio. This permits a significant reduction in the dose of FT required to achieve a therapeutic effect. Other pyridimines, including uridine, thymidine, thymine, and cytosine are either less effective than uracil or no better in potentiating the antitumor efficacy of FT without unacceptably potentiating toxicity. Potent synthetic inhibitors of dihydropyrimidine dehydrogenase (DHPDHase) have also been utilized with FT or 5FU. 5-chloro-2,6-dihydroxypyridine (CDHP) is more potent than uracil as an inhibitor of DHPDHase. However, this compound also enhances the toxicity of 5FU, so that, in its intended clinical implementation, a third component, oxonic acid, is co-administered to reduce the intestinal toxicity.

Several investigators have administered pyrimidines with 5FU attempting to improve the therapeutic index of this antineoplastic agent. In vivo, uridine and thymidine when administered at the same time as 5FU increased both the antitumor efficacy of 5FU and its toxicity, so that there was no net increase in therapeutic index (Hartman and Bollag, *Med. Oncol. & Tumor Pharmacother.*, 3:111-118 [1986]). Burchenal et al. (*Cancer Chemother. Rep.*, 6:1-5 [1960]) summarized comprehensive studies on interactions of 5FU and 5-fluorodeoxyuridine (FUDR) and pyrimidine compounds. They noted that despite the fact that pyrimidines and pyrimidine nucleosides, at doses which are inactive alone, markedly potentiate the antileukemic effects of small doses of FUDR or FU, it has not been possible with any combination to improve significantly and with any degree of regularity the results which can be obtained with maximum tolerated doses of FU or FUDR alone. Similarly, Jato et al. (*J. Pharm Sci.*, 64:943-945 [1975]), in an investigation of combinations of deoxyuridine with 5FU and FUDR report that any therapeutic benefit of the combination therapy could be duplicated with either 5FU or FUDR at a higher dose. Although deoxyuridine, by inhibiting the catabolism of the fluoropyrimidines permitted administration of lower doses, deoxyuridine there was no improvement in antitumor activity at equitoxic doses of the combination versus FU or FUDR alone.

As in the case of uridine, problems of poor bioavailability after oral administration limit the clinical utility of administration of deoxycytidine, cytidine, and deoxyuridine themselves for modulation of toxicity of chemotherapy agents.

Arabinosyl cytosine (Ara-C) is an important agent in the treatment of leukemia, and is also useful as an immunosuppressant. Bone marrow toxicity (myeloid and erythroid) associated with Ara-C administration can be partially prevented by administration of deoxycytidine (Belyanchikova et al. *Bull. Exp. Biol. Med.* 91:83-85 [1981]), while the toxicity of Ara-C to lymphocytes is not as strongly attenuated by deoxycytidine. In cell cultures, normal myeloid progenitor cells are protected from Ara-C by deoxycytidine better than are leukemic cells (K. Bhalla et al. *Blood* 70:568-571 [1987]). Deoxycytidine also attenuates toxicity of 5-aza-2'-deoxycytidine and arabinosyl 5-azacytosine in cell cultures (K. Bhalla et al. *Leukemia* 1:814-819 [1987]). Prolonged (5 day) infusion of high doses of deoxycytidine via a central venous catheter was proposed as a means for clinical implementation of modulation of Ara-C toxicity with deoxycytidine (K. Bhalla et al. *Leukemia* 2:709-710 [1988]).

N-phosphonoacetyl-L-aspartic acid (PALA) is an antineoplastic agent that inhibits the enzyme aspartate transcarbamoylase, an enzyme indirectly involved in biosynthesis of pyrimidine nucleotides. Side effects of PALA primarily involve damage to gastrointestinal toxicity and mucositis. Pyrazofurin (a carbon linked pyrimidine analog), 6-azauridine, and 6-azacytidine all interfere with pyrimidine nucleotide synthesis and metabolism.

3'-Azidodeoxythymidine (AZT) is used clinically, in patients infected with Human Immunodeficiency Virus (HIV, the infectious agent in AIDS). AZT prolongs the lifespan of patients infected with HIV, but also impairs hematopoiesis, producing leukopenia and anemia. In cell cultures, uridine ameliorates AZT-induced toxicity to granulocyte/macrophage progenitor cells without impairing the antiviral actions of AZT (Sommadossi et al., (1988) Antimicrobial Agents and Chemotherapy, 32:997-1001); thymidine attenuated both toxicity and antiviral activity. In mice, parenteral administration of high doses of uridine provided some amelioration of AZT-induced anemia, but only at uridine doses which increased mortality during the study; a low, non-toxic dose of uridine (500 mg/kg/d) did not reduce AZT-induced hematologic toxicity (A. Falcone, et al. *Blood* 76:2216-21 [1990]). Sommadossi and el Kouni (U.S. Pat. No. 5,077,280) proposed the administration of uridine by periodic intravenous injection in order to attenuate AZT toxicity. Bhalla et al. (*Blood* 74:1923-1928 [1989]) reported that deoxycytidine protects normal human bone marrow progenitor cells in vitro against the cytotoxicity of AZT with preservation of antiretroviral activity.

5-Fluoroorotate, an analog of the pyrimidine nucleotide precursor orotic acid, has antiproliferative effects on human cells, but is especially useful for treating infections with malarial parasites, e.g., *Plasmodium yoelii* or *Plasmodium falciparum*, which are dependent on de novo pyrimidine biosynthesis. Administration of uridine to mice treated with 5-fluoroorotate attenuated host toxicity due to the latter without impairing its antimalarial activity (Z M Gomez and P K Rathod, *Antimicrob. Agents Chemother.* 34:1371-1375 ('1490).

Dideoxycytidine (ddC) is also useful against retroviral infections including HIV; side effects of ddC include peripheral neuropathy, mouth ulcers, and reduced platelet counts. The toxicity of ddC on human myeloid progenitor cells in culture can be ameliorated by deoxycytidine without thereby impairing the antiretroviral efficacy of ddC (K. Bhalla et al., *AIDS* 4:427-31 [1990]).

The methods disclosed in the prior art cited above for administering these pyrimidine nucleosides to modify chemotherapy in the clinical setting are neither practical (prolonged infusion of deoxycytidine or uridine via a central venous catheter requires hospitalization, risk of infection, and discomfort to the patient) or satisfactory (orally administered uridine is poorly absorbed; therapeutically adequate doses of oral uridine produce diarrhea).

Commonly owned U.S. Pat. No. 438,493 demonstrates the use of acylated derivatives of cytidine and uridine to increase blood cytidine or uridine levels.

Some acyl derivatives of pyrimidine nucleosides have been synthesized for use as protected intermediates in the synthesis of oligonucleotides or nucleoside analogs, e.g. 5'-O-benzoyluridine, triacetylcytidine, and triacetyluridine. See Sigma Chemical Company 1991 catalog, pages 155, 980, and 981 respectively.

OBJECTS OF THE INVENTION

It is a primary object of this invention to provide a method for effectively preventing or treating toxic symptoms of antiviral or anticancer chemotherapy, including but not limited to damage to the hematopoietic system and to gastrointestinal mucosa.

A further object of the invention is to provide compounds and methods to permit administration of higher doses of the chemotherapy agents.

A further object of the invention is to provide methods of increasing blood and tissue levels of uridine and cytidine, and their corresponding deoxyribonucleosides deoxycytidine and deoxyuridine through oral administration of a compound or compounds.

A further object of the invention is to provide a method for preventing or ameliorating gastrointestinal epithelium damage due to cytotoxic chemotherapy agents.

SUMMARY OF THE INVENTION

These and other objects of the invention are achieved by oral or parenteral administration of acylated derivatives of non-methylated pyrimidine nucleosides, e.g. acylated derivatives of uridine, deoxyuridine, cytidine, or deoxycytidine, which are administered to animals, including mammals such as humans. The administration of these compounds alone, or in combination, is useful in preventing or ameliorating toxic effects of cytoreductive chemotherapy in animals.

Thus, the compounds of the invention, alone or in combinations, are useful in the treatment of disorders of hematopoiesis induced by chemical agents; are useful as adjuncts to cancer and antiviral chemotherapy; and are useful for the treatment of other pathological conditions.

An important aspect of this invention is the discovery that acyl derivatives of non-methylated pyrimidine nucleosides have unexpected therapeutic properties.

COMPOUNDS OF THE INVENTION

In all cases except where indicated, letters and letters with subscripts symbolizing variable substituents in the chemical structures of the compounds of the invention are applicable'only to the structure immediately preceding the description of the symbol.

The compounds useful in attenuating toxicity due to anticancer or antiviral agents have the following general structures:

(1) An acyl derivative of uridine having the formula:

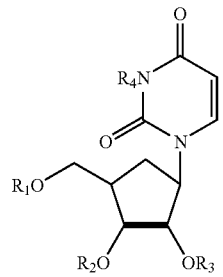

wherein $R_1$, $R_2$, $R_3$, and $R_4$ are the same or different and each is hydrogen or an acyl radical of a metabolite, provided that at least one of said R substituents is not hydrogen, or a pharmaceutically acceptable salt thereof.

(2) An acyl derivative of cytidine having the, formula:

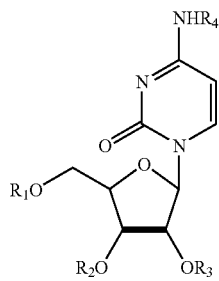

wherein $R_1$, $R_2$, $R_3$, and $R_4$ are the same or different and each is hydrogen or an acyl radical of a metabolite, provided that at least one of said R substituents is not hydrogen, or a pharmaceutically acceptable salt thereof.

(3) An acyl derivative of deoxycytidine having the formula:

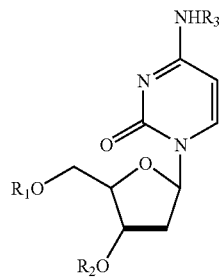

wherein $R_1$, $R_2$, and $R_3$ are the same or different and each is hydrogen or an acyl radical of a metabolite, provided that at least one of said R substituents is not hydrogen, or a pharmaceutically acceptable salt thereof.

(4) An acyl derivative of deoxyuridine having the formula:

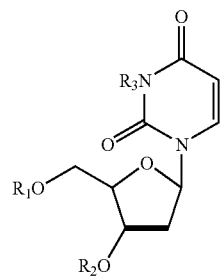

wherein $R_1$, $R_2$, and $R_3$ are the same or different and each is hydrogen or an acyl radical of a metabolite, provided that at least one of said R substituents is not hydrogen, or a pharmaceutically acceptable salt thereof.

Compounds of the invention useful in ameliorating toxicity due to anticancer or antiviral chemotherapy agents include the following:

(5) An acyl derivative of uridine having the formula:

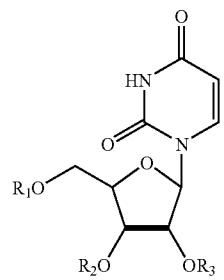

wherein $R_1$, $R_2$ and $R_3$ are the same, or different, and each is hydrogen or an acyl radical of
   a. an unbranched fatty acid with 5 to 22 carbon atoms,
   b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine, c. a dicarboxylic acid having 3-22 carbon atoms, d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(6) An acyl derivatives of cytidine having the formula:

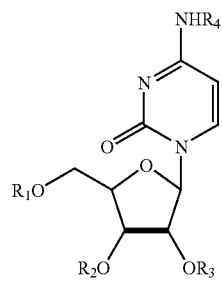

wherein $R_1$, $R_2$, $R_3$, and $R_4$ are the same, or different, and each is hydrogen or an acyl radical of
  a. an unbranched fatty acid with 5 to 22 carbon atoms,
  b. an amino acid selected from the group consisting of glycine, the L forms of phenylalanine, alanine, valine, leucine, isoleucine, tyrosine, proline, hydroxyproline, serine, threonine, cystine, cysteine, aspartic acid, glutamic acid, arginine, lysine, histidine carnitine and ornithine,
  c. a dicarboxylic acid having 3-22 carbon atoms,
  d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(7) An acyl derivative of deoxycytidine, having the formula

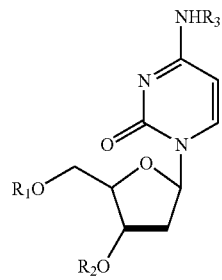

wherein $R_1$, $R_2$, and $R_3$ are the same, or different, and each is hydrogen or an acyl radical derived from
  a. an unbranched fatty acid with 3 to 22 carbon atoms,
  b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine,
  c. nicotinic acid
  d. a dicarboxylic acid having 3-22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

(8) An acyl derivative of deoxyuridine, having the formula

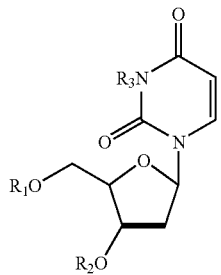

wherein $R_1$, $R_2$, and $R_3$ are the same, or different, and each is hydrogen or an acyl radical derived from
  a. an unbranched fatty acid with 3 to 22 carbon atoms,
  b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine,
  c. nicotinic acid
  d. a dicarboxylic acid having 3-22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

(9) An acyl derivative of uridine having the formula:

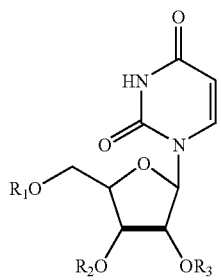

wherein at least one of $R_1$, $R_2$, or $R_3$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(10) An acyl derivative of cytidine having the formula:

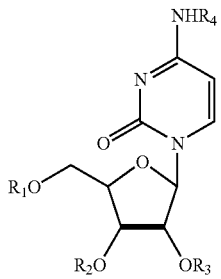

wherein at least one of $R_1$, $R_2$, $R_3$ or $R_4$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(11) An acyl derivative of deoxycytidine having the formula:

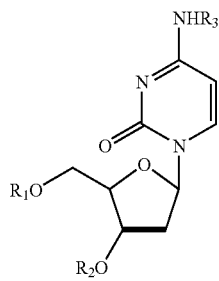

wherein at least one of $R_1$, $R_2$, or $R_3$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(12) An acyl derivative of deoxyuridine having the formula:

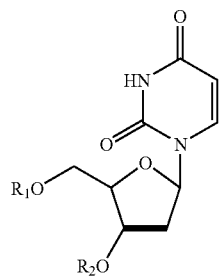

wherein at least one of $R_1$ or $R_2$ is a hydrocarbyloxycarbonyl moiety containing 2-26 carbon atoms and the remaining R substituents are independently a hydrocarbyloxycarbonyl or hydrocarbylcarbonyl moiety or H or phosphate.

The invention, as well as other objects, features and advantages thereof will be understood more clearly and fully from the following detailed description, when read with reference to the accompanying results of the experiments discussed in the examples below.

DETAILED DESCRIPTION OF THE INVENTION

The subject invention relates to the use of acylated derivatives of non-methylated pyrimidine nucleosides, i.e. acylated derivatives of uridine, deoxyuridine, cytidine, or deoxycytidine, such as triacetyluridine (TAU), to attenuate toxicity of chemotherapeutic agents and antiviral agents in vivo. The invention also relates to the administration of these pyrimidine nucleoside compounds, alone or in combinations, with or without other agents, to animals.

In the case of many antineoplastic and antiviral chemotherapy agents, exposure of affected cells to appropriate natural nucleosides can prevent or ameliorate damage to those cells. The compounds and methods of the subject invention make it possible to reduce toxicity while maintaining therapeutic efficacy of the antiviral or antineoplastic agent, and conversely, to increase the dose of the chemotherapeutic agent while maintaining an acceptable degree of toxicity.

The present invention provides compounds and methods for treating or preventing toxic symptoms of antiviral or anti- cancer chemotherapy through oral or parenteral administration of acyl derivatives of non-methylated pyrimidine nucleosides.

A. DEFINITIONS

The term "non-methylated pyrimidine nucleoside" as used herein means naturally occurring nucleosides other than thymidine (5-methyldeoxyuridine) or 5-methylcytidine and other similar naturally-occurring methylated nucleosides. Examples of non-methylated pyridimidine nucleosides include uridine, cytidine, deoxyuridine, and deoxycytidine.

The term "acyl derivative" as used herein means a derivative of a non-methylated pyrimidine nucleoside in which a substantially nontoxic organic acyl substituent derived from a carboxylic acid is attached to one or more of the free hydroxyl groups of the ribose moiety of a non-methylated pyrimidine nucleoside with an ester linkage and/or where such a substituent is attached to the amine substituent on the pyrimidine ring of cytidine or deoxycytidine, with an amide linkage. Such acyl substituents are derived from carboxylic acids which include, but are not limited to, compounds selected from the group consisting of a fatty acid, an amino acid, nicotinic acid, dicarboxylic acids, lactic acid, p-aminobenzoic acid and orotic acid. Advantageous acyl substituents are carboxylic acids which are normally present in the body, either as dietary constituents or as intermediary metabolites.

The term "analog" as used herein means a nucleoside chemically modified in either the pyrimidine ring or the ribose (or deoxyribose) moiety by a means other than acylation or attachment of other biologically labile substituents (e.g. phosphorylation of hydroxyl groups on the sugar). Specifically, nucleoside analogs, in the context of this invention, are drugs with structural similarities to the naturally occurring nucleosides, but with antiviral, antineoplastic, or cytotoxic properties. Examples of antineoplastic nucleoside analogs include but are not limited to the following: 5-fluorouracil (5-FU), 5-FU prodrugs (e.g. ftorafur, 5'-deoxyfluorouridine, carmofur), fluorouridine, 2'-deoxyfluorouridine, prodrug derivatives of fluorouridine or 2'-deoxyfluorouridine, fluorocytosine, arabinosyl cytosine, prodrugs of arabinosyl cytosine, cyclocytidine, 5-aza-2'-deoxycytidine, arabinosyl 5-azacytosine, 6-azauridine, azaribine, 6-azacytidine, trifluoro-methyl-2'-deoxyuridine, thymidine, and 3-deazauridine. Examples of antiviral nucleoside analogs include but are not limited to the following: 5-ethyl-2'-deoxyuridine, 5-iodo-2'-deoxyuridine, 5-bromo-2'-deoxyuridine, 5-methylamino-2'-deoxyuridine, arabinosyluracil, dideoxyuridine, dideoxycytidine, 2',3'-dideoxycytidin-2'-ene, 3'-deoxythymidin-2'-ene, 3'-azido-2',3'-dideoxyuridine, and 3'-azidodeoxythymidine (AZT). Analogs of pyrimidine nucleoside precursors, e.g. N-phosphonoacetyl-L-aspartic acid (PALA), are encompassed by this term.

Some nucleoside analogs are considered to have structural similarities to particular naturally-occurring nucleosides. In the context of the compounds of the invention, nucleoside analogs are divided into cytidine analogs if they have an exocyclic amino group in the 4 position of the pyrimidine ring (an amino group in that position signifies the distinction between cytidine and uridine). Nucleoside analogs that are specifically analogs of cytidine include but are not limited to: fluorocytosine, arabinosyl cytosine, prodrugs of arabinosyl cytosine, cyclocytidine, 5-aza-2'-deoxycytidine, arabinosyl 5-azacytosine, 6-azacytidine, and dideoxycytidine. Nucleoside analogs that are specifically considered to be analogs of uridine include but are not limited to: 5-fluorouracil (5-FU), 5-FU prodrugs (e.g. ftorafur, 5'-deoxyfluorouridine, carmofur), fluorouridine, 2'-deoxyfluorouridine, prodrug derivatives of fluorouridine, prodrug derivatives of 2'-deoxyfluorouridine, trifluoromethyl-2'-deoxyuridine, 6-azauridine, azaribine, 3-deazauridine, 5-ethyl-2'-deoxyuridine, 5-iodo-2'-deoxyuridine, 5-bromo-2'-deoxyuridine, 5-methylamino-2'-deoxyuridine, arabinosyluracil, and dideoxyuridine. Some cytotoxic nucleoside analogs are also specifically analogs of thymidine, e.g. AZT.

The term "pharmaceutically acceptable salts" as used herein means salts with pharmaceutically acceptable acid addition salts of the derivatives, which include, but are not limited to, sulfuric, hydrochloric, or phosphoric acids.

The term "coadministered" as used herein means that at least two of the compounds of the invention are administered during a time frame wherein the respective periods of pharmacological activity overlap.

The term "hydrocarbylcarbonyl" as used herein means an acyl radical of a carboxylic acid in which the atom adjacent to the carbonyl carbon atom is another carbon atom. The parent carboxylic acid may, for example, be a fatty acid, an aromatic acid (e.g. benzoate, nicotinoate, or their congeners), an amino acid, a cycloalkylcarboxylic acid, or a dicarboxylic acid.

The term "hydrocarbyloxycarbonyl" as used herein means an acyl radical of a carboxylic acid in which the atom adjacent to the carbonyl carbon atom is oxygen which is furthermore covalently linked to another carbon atom. This can also be described as a radical of a carbonate ester of an alcohol, which, when cleaved from a non-methylated pyrimidine nucleoside following administration, degrades further into carbon dioxide and an alcohol. Advantageous alcohols are those which are of low toxicity, particularly those which enter readily into normal metabolic or eliminative pathways.

The term "fatty acids" as used herein means aliphatic carboxylic acids having 2-22 carbon atoms. Such fatty acids may be saturated, partially saturated or polyunsaturated.

The term "amino acids" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids.

The term "dicarboxylic acids" as used herein means fatty acids with a second carboxylic acid substituent.

The term "therapeutically effective amount" as used herein refers to that amount which provides therapeutic effects for a given condition and administration regime.

B. COMPOUNDS OF THE INVENTION

In all cases except where indicated, letters and letters with subscripts symbolizing variable substituents in the chemical structures of the compounds of the invention are applicable only to the structure immediately preceding the description of the symbol.

The compounds useful in attenuating toxicity due to anticancer or antiviral agents have the following general structures:

(1) An acyl derivative of uridine having the formula:

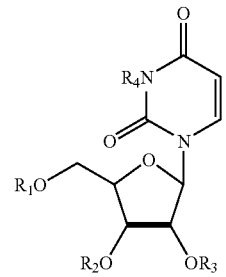

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

(2) An acyl derivative of cytidine having the formula:

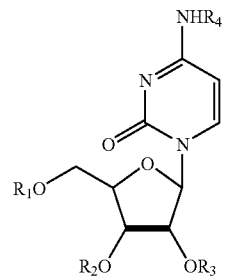

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

(3) An acyl derivative of deoxycytidine having the formula:

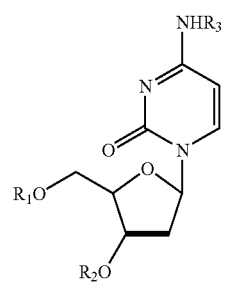

wherein $R_1$, $R_2$, and $R_3$ are the same or different and each is hydrogen or an acyl radical of a metabolite, provided that at least one of said R substituents is not hydrogen, or a pharmaceutically acceptable salt thereof.

(4) An acyl derivative of deoxyuridine having the formula:

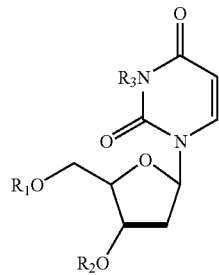

wherein $R_1$, $R_2$, and $R_3$ are the same or different and each is hydrogen or an acyl radical of a metabolite, provided that at least one of said R substituents is not hydrogen, or a pharmaceutically acceptable salt thereof.

Compounds of the invention useful in ameliorating toxicity due to anticancer or antiviral chemotherapy agents include the following:

(5) An acyl derivative of uridine having the formula:

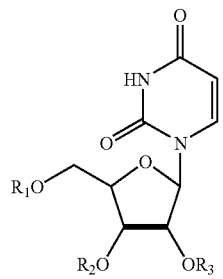

wherein $R_1$, $R_2$, and $R_3$ are the same, or different, and each is hydrogen or an acyl radical of
  a. an unbranched fatty acid with 5 to 22 carbon atoms,
  b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine,
  c. a dicarboxylic acid having 3-22 carbon atoms,
  d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(6) An acyl derivatives of cytidine having the formula:

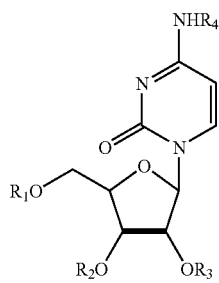

wherein $R_1$, $R_2$, $R_3$, and $R_4$ are the same, or different, and each is hydrogen or an acyl radical of
  a. an unbranched fatty acid with 5 to 22 carbon atoms,
  b. an amino acid selected from the group consisting of glycine, the L forms of phenylalanine, alanine, valine, leucine, isoleucine, tyrosine, proline, hydroxyproline, serine, threonine, cystine, cysteine, aspartic acid, glutamic acid, arginine, lysine, histidine carnitine and ornithine,
  c. a dicarboxylic acid having 3-22 carbon atoms,
  d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(7) An acyl derivative of deoxycytidine, having the formula

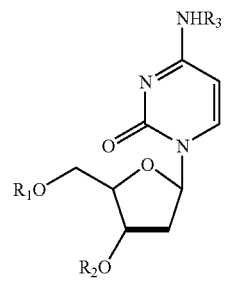

wherein $R_1$, $R_2$, and $R_3$ are the same, or different, and each is hydrogen or an acyl radical derived from
  a. an unbranched fatty acid with 3 to 22 carbon atoms,
  b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine,
  c. nicotinic acid
  d. a dicarboxylic acid having 3-22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

(8) An acyl derivative of deoxyuridine, having the formula

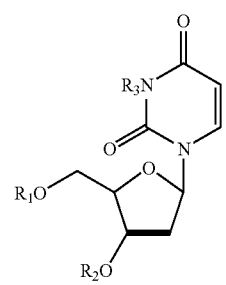

wherein $R_1$, $R_2$, and $R_3$ are the same, or different, and each is hydrogen or an acyl radical derived from
  a. an unbranched fatty acid with 3 to 22 carbon atoms,
  b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine, c. nicotinic acid d. a dicarboxylic acid having 3-22 carbon atoms, provided that not all of $R_1$, $R_2$, and $R_3$ are H, and where $R_3$ is not H, then $R_1$ and/or $R_2$ may also be acetyl, or a pharmaceutically acceptable salt thereof.

(9) An acyl derivative of uridine having the formula:

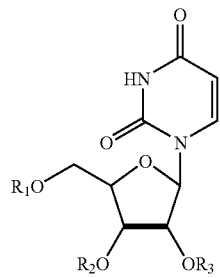

wherein at least one of $R_1$, $R_2$, or $R_3$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(10) An acyl derivative of cytidine having the formula:

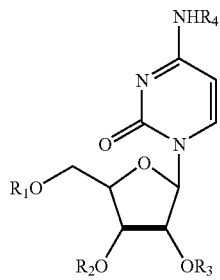

wherein at least one of $R_1$, $R_2$, $R_3$ or $R_4$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(11) An acyl derivative of deoxycytidine having the formula:

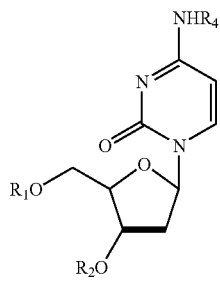

wherein at least one of $R_1$, $R_2$, or $R_3$ is a hydrocarbyloxycarbonyl moiety containing 2-26 carbon atoms and the remaining R substituents are independently a hydrocarbyloxycarbonyl or hydrocarbylcarbonyl moiety or H or phosphate.

(12) An acyl derivative of deoxyuridine having the formula:

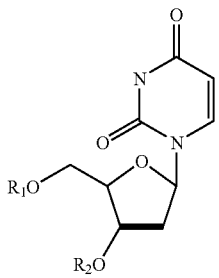

wherein at least one of $R_1$ or $R_2$ is a hydrocarbyloxycarbonyl moiety containing 2-26 carbon atoms and the remaining R substituents are independently a hydrocarbyloxycarbonyl or hydrocarbylcarbonyl moiety or H or phosphate.

Also encompassed by the invention are the pharmaceutically acceptable salts of the above-noted compounds.

Advantageous compounds of the invention are fatty acid esters of uridine and deoxycytidine, especially those with 4 or fewer carbon atoms in the acyl substituent. Particularly advantageous compounds are fatty acid esters of uridine or deoxycytidine with 2 or 3 carbon atoms in the acyl substituent.

Other advantageous compounds of the invention are hydrocarbyloxycarbonyl derivatives of uridine and deoxycytidine, particularly those with 3 to 6 carbon atoms in the hydrocarbyloxycarbonyl moiety.

In one embodiment of the invention, prodrugs of the compounds of the invention with enhanced water solubility are prepared by attaching phosphate to a free hydroxyl group on the aldose moiety of the acylated non-methylated pyrimidine nucleoside.

C. COMPOSITIONS OF THE INVENTION

Compositions of the invention include one or more of the above-noted compounds along with a pharmaceutically acceptable carrier.

In another embodiment, the compositions of the invention include in addition to one or more compounds of the invention and at least one of the following agents which enhance hematopoiesis: oxypurine nucleosides, congeners of oxypurine nucleosides, and acyl derivatives of oxypurine nucleosides and their congeners, e.g. fatty acid esters of guanosine or deoxyguanosine (see U.S. Pat. No. 653,882, filed, Feb. 8, 1991, hereby incorporated by reference), a nonionic surfactant, an interleukin such as IL-1, -2, -3, -4, -5, -6, -7, -8 (advantageously IL-1,3, or 6), a colony-stimulating factor, for example granulocyte colony-stimulating factor (G-CSF), granulocyte/macrophage colony-stimulating factor (GM-CSF), stem cell factor (SCF), erythropoietin (EPO), glucan, polyinosine-polycytidine, or any other agent having beneficial effects on hematopoiesis.

Acyl derivatives of oxypurine nucleosides which enhance hematopoiesis and which are optionally administered in conjunction with the compounds of the invention have the following general structure:

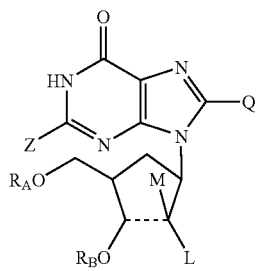

$R_A$=H or an acyl radical of a carboxylic acid with 2 to 30 carbon atoms, and $R_B$=H or an acyl radical of a carboxylic acid with 2 to 30 carbon atoms, and Z=H, OH, =O, or $NHR_C$ where $R_C$=H or an acyl radical of a carboxylic acid with 2 to 30 carbon atoms, and L=H or $OR_D$, where $R_D$=H or an acyl radical of a carboxylic acid with 2 to 30 carbon atoms, and M=H or $OR_E$, where $R_E$=H or an acyl radical of a carboxylic acid with 2 to 30 carbon atoms, with the proviso that at least one of L and M is H, and Q=H, a halogen, $NHR_F$ where $R_F$ is H or an acyl or alkyl radical containing 1 to 10 carbon atoms, S divalently bound to the carbon in which case the adjacent carbon-nitrogen double bond is a single bond and an H is then attached to that nitrogen, $SR_G$ where $R_G$ is H or an acyl or alkyl radical containing 1 to 10 carbon atoms, O divalently bound to the carbon, in which case the adjacent carbon-nitrogen double bond is a single bond and an H is then attached to that nitrogen, or $OR_H$ where $R_H$ is H or an acyl or alkyl radical containing 1 to 10 carbon atoms, and the C—C bond between the 2' and 3' positions of the aldose moiety is optionally present.

In another embodiment of the invention, an acylated non-methylated pyrimidine nucleoside is formulated with a compound capable of enhancing the uptake and phosphorylation of nucleosides into cells such as insulin or an insulinogenic carbohydrate.

In another embodiment of the invention, the composition comprises at least one compound of the invention and an antiviral or antineoplastic agent (see detailed discussion of these agents in the section below entitled Therapeutic Uses of the Compounds and Compositions of the Invention).

In another embodiment, the compositions of the invention comprise an acyl derivative of uridine or deoxyuridine and a compound capable of inhibiting uridine phosphorylase. Uridine phosphorylase is the primary enzyme involved in the catabolism of uridine, forming uracil and ribose phosphate. Administration of a compound which inhibits uridine phosphorylase will modify the pharmacokinetics and biological activity of uridine or deoxyuridine produced by deacylation of acylated derivatives of these two non-methylated pyrimidine nucleosides. Examples of suitable inhibitors of uridine phosphorylase include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl]barbiturate, 5-benzyloxybenzylacetyl-1-[(1-hydroxy-2-ethoxy)methyl]barbiturate, and 5-methoxybenzylacetylacyclobarbiturate, 2,2'-anhydro-5-ethyluridine, and acyclouridine compounds, particularly 5-benzyl substituted acyclouridine congeners including but not limited to benzylacyclouridine, benzyloxybenzylacyclouridine, aminomethyl-benzylacyclouridine, aminomethyl-benzyloxybenzylacyclouridine, hydroxymethyl-benzylacyclouridine, and hydroxymethyl-benzyloxybenzyl-acyclouridine. See also WO 89/09603 and WO 91/16315, hereby incorporated by reference.

In another embodiment of the invention, the composition comprises an acyl derivative of a non-methylated pyrimidine nucleoside and a compound which inhibits cellular uptake or excretion of non-methylated pyrimidine nucleosides, and thereby promotes maintenance of blood nucleoside levels after enzymatic deacylation of administered doses of acylated derivatives of non-methylated pyrimidine nucleosides. Such modulators of uridine transport or excretion include but are not limited to dipyridamole, probenicid, lidoflazine or nitrobenzylthioinosine.

In another embodiment of the invention, the composition comprises an acyl derivative of cytidine and a compound capable of inhibiting the enzyme uridine phosphorylase. Inhibition of this enzyme is useful in conjunction with cytidine since cytidine is in part deaminated in the bloodstream after deacylation of its acyl derivatives, providing uridine to the tissues.

In another embodiment of the invention, the composition comprises an acyl derivative of cytidine or deoxycytidine and a compound capable of inhibiting deoxycytidine deaminase. By inhibiting the deamination of deoxycytidine or cytidine, inhibitors of cytidine deaminase or deoxycytidine deaminase such as tetrahydrouridine or tetrahydro-2'-deoxyuridine modify the efficacy of acyl derivatives of cytidine or deoxycytidine. In another embodiment of the invention, an inhibitor of cytidine deaminase or deoxycytidine deaminase is used to modify the toxicity of an antiviral or anticancer nucleoside analog (see Example 11).

In another embodiment of the invention, especially for prevention or treatment of damage to the gastrointesinal mucosa, the composition comprises an acyl derivative of a non-methylated pyrimidine nucleoside and an agent or agents with utility in promoting mucosal healing or in reducing discomfort. Examples of such agents include but are not limited to sucralfate, mixtures of two or more deoxyribonucleosides as disclosed in U.S. Pat. No. 341,925, filed Apr. 21, 1989 (hereby incorporated by reference), allopurinol, antibiotics like chlorhexidine gluconate or local anesthetics like benzocaine.

In another embodiment of the invention, the composition comprises a combination of an acyl derivative of a non-methylated pyrimidine nucleoside and an orally-active antineoplastic nucleoside analog. An advantageous combination is an acyl derivative of uridine with an orally active fluorinated pyrimidines, especially prodrugs of 5-fluorouracil. In such compositions, the acyl derivative of a non-methylated pyrimidine nucleoside is mixed with (or otherwise adminstered with) the antineoplastic nucleoside analog in molar ratios, ranging from 1:1 to 12:1. Molar ratios ranging from 2:1 to 8:1 are generally advantageous. Suitable orally-active fluorinated pyrimidines include Tegafur, 5'-deoxyfluorouridine, 5-fluorouracil, 5-fluorouridine, 2'-deoxy-5-fluorouridine, $N^4$-trimethoxybenzoyl-5'-deoxy-5-fluorocytidine, or acyl derivatives thereof.

The compositions, depending on the intended use, are manufactured in the form of a liquid, a suspension, a tablet, a capsule, a dragee, an injectable solution, a topical solution, or a suppository (see discussion of formulation below).

As an alternative to formulation of compositions containing a compound of the invention and another active agent (as discussed above), in another embodiment, the compounds of the invention are coadministered with the other active agents.

D. THERAPEUTIC USES OF THE COMPOUNDS AND COMPOSITIONS OF THE INVENTION

The compounds of the invention are useful to prevent or treat damage to the process of hematopoiesis and immune system function in animals. The compounds reduce damage to the process of hematopoiesis by minimizing loss in blood cell counts after bone marrow damage or suppression caused by antiviral or antineoplastic agents which affect nucleotide biosynthesis, metabolism, or utilization. The compounds of the invention are useful in treating humans; however, the invention is not intended to be so limited, it being within the contemplation of the invention to treat all animals that experience a beneficial effect from the administration of the active compounds of the invention.

The invention is furthermore embodied in the administration of a pharmaceutical compound or composition of the invention, or in combinations, for the purpose of preventing, attenuating, or ameliorating toxicity associated with administration of antiviral or antineoplastic agents which affect nucleotide biosynthesis, metabolism, or utilization.

Specific conditions where advantages are achieved using the compounds, compositions, and methods of the invention include situations where the hematopoietic system has suffered or is likely to suffer damage from chemotherapy, particularly chemotherapy that affects nucleotide biosynthesis, metabolism, or utilization. Such conditions include treating animals, e.g. human patients, subjected to cytoreductive cancer chemotherapy or antiviral chemotherapy. Specifically included are veterinary applications requiring maintenance of blood cell counts.

The compounds and compositions are also useful for preventing or treating damage caused by anticancer or antiviral chemotherapy agents to other tissues, including but not limited to gastrointestinal epithelium. For this purpose, the compounds and compositions are optionally administered orally, as a suppository, or parenterally.

By attenuating damage to the hematopoietic and immune systems caused by anticancer or antiviral chemotherapy, the compounds and methods of the invention reduce the risk of susceptibility to opportunistic or secondary infections (bacterial, viral, or fungal).

The efficacy of the compounds of the invention is enhanced by coadministration of agents which stimulate the uptake and phosphorylation of pyrimidine nucleosides by cells. Such agents include hematopoietic growth factors (e.g. G-CSF, GM-CSF, SCF, acylated oxypurine nucleosides and their congeners, erythropoietin, and interleukins), insulin, and insulinogenic carbohydrates such as glucose or glucose polymers.

Treatment of Complications Associated with Cancer Chemotherapy

The white blood cell counts, and particularly the neutrophil counts, of patients treated with standard anti-neoplastic chemotherapy agents (e.g., 5-fluorouracil, fluorodeoxyuridine, vinca alkaloids, cyclophosphamide and other nitrogen mustard alkylating agents, daunorubicin, doxorubicin, methotrexate, cytosine arabinoside, 6-mercaptopurine, thioguanosine, podophyllotoxins, cisplatin or combinations of such cytoreductive agents) are often greatly diminished. In the case of cytotoxic agents which act by affecting nucleotide biosynthesis, metabolism, or utilization, daily administration (oral or parenteral) of an effective dose, (for example, 0.1-10.0 grams) of a compound of the invention such as triacetyluridine (or other acyl derivatives of uridine, cytidine, deoxycytidine, or deoxyuridine) for several days reduces the severity of the neutropenia which typically occurs several days to several weeks after chemotherapy is initiated. This reduces the likelihood of infection throughout the course of treatment, and makes it possible for the patient to receive larger doses of the chemotherapeutic agents and/or to receive repeated doses sooner than comparable patients not treated with the uridine derivative(s). Similarly, chemotherapy-induced alterations in counts of other blood cell types (lymphocytes, platelets, erythrocytes, etc.) are ameliorated by administration of the compounds and compositions of the invention.

Antineoplastic agents with which the compounds and methods of the invention are particularly useful include: 5-fluorouracil (5-FU), 5-FU prodrugs (e.g. ftorafur, 5'-deoxyfluorouridine, carmofur), fluorouridine, 2'-deoxyfluorouridine, prodrug derivatives of fluorouridine or 2'-deoxyfluorouridine, fluorocytosine (which also has antifungal activity), arabinosyl cytosine, prodrugs of arabinosyl cytosine, cyclocytidine, 5-aza-2'-deoxycytidine, arabinosyl 5-azacytosine, N-phosphonoacetyl-L-aspartic acid (PALA), pyrazofurin, 6-azauridine, azaribine, 6-azacytidine, trifluoro-methyl-2'-deoxyuridine, thymidine, and 3-deazauridine. Such antineoplastic agents and various other therapeutic nucleoside analogs act by affecting nucleoside or nucleotide biosynthesis, utilization, or metabolism; hence, amelioration of their toxic effects is accomplished by administration of the pyrimidine compounds of the invention.

The compounds of the invention are administered before, during, and/or after administration of the anti-neoplastic or antiviral agents. Typically, the compounds of the invention are administered after a dose of a cancer chemotherapy agent, as a means of "rescuing" normal tissues after administration of an effective antineoplastic dose of the agent.

Gastrointestinal epithelium is sensitive to cancer chemotherapy agents like fluorouracil. Mucositis, stomatitis, or ulceration of the gastrointestinal mucosa are common side effects of cancer chemotherapy, resulting in discomfort, diarrhea, electrolyte imbalances and weight loss. The compounds of and compositions of the invention are useful in preventing or treating damage to the gastrointestinal tract (including the mouth) caused by cancer chemotherapy agents. The compounds and compositions of the invention are optionally administered for this purpose as a solution or suspension in liquid form (as a mouthwash, as a composition to be swallowed, or as an enema), as a capsule, dragee, or tablet, as an injectable solution, or as a suppository. Systemic administration of the compounds and compositions of the invention also reduces damage to gastrointestinal mucosa caused by anticancer or antiviral nucleoside analogs.

Topical application of the compounds (e.g. to the scalp) of the invention is useful for preventing chemotherapy-induced alopecia.

Acyl derivatives of uridine are advantageous in preventing or treating toxicity due to fluorouracil or related fluorinated analogs of uridine (e.g. fluorouridine or prodrugs thereof, fluorodeoxyuridine or prodrugs thereof, ftorafur, 5'-deoxyfluorouridine). For oral administration, advantageous acyl derivatives of uridine are those substituted with short-chain fatty acids, (especially acetate) or with short chain carbyloxycarbonates (e.g. ethoxycarbonate). Acyl derivatives of cytidine or deoxyuridine are also useful in treating toxicity due to fluorouracil or related fluorinated pyrimidine analogs.

In a typical therapeutic situation, a patient receives a dose of fluorouracil, either as a single treatment agent or as part of a regimen also involving administration of other antineoplastic drugs like methotrexate, leucovorin, PALA, or cyclophosphamide. Several hours to one day after administration of the 5-FU, the patient receives an oral dose of 1 to 10 grams of triacetyluridine. The patient receives additional doses of 5-FU of similar size every 6 to 8 hours over the course of the next 2 to 4 days. The patient may receive additional courses of 5-FU plus TAU on a weekly basis or less frequently.

Acyl derivatives of uridine and, secondarily, cytidine, are also advantageous for treatment or prevention of toxicity due to N-phosphonoacetyl-L-aspartic acid (PALA), pyrazofurin, 6-azauridine, azaribine, trifluoro-methyl-2'-deoxyuridine, and 3-deazauridine.

For modulating toxicity and efficacy of orally-active antineoplastic drugs, particularly orally-active fluorinated pyrimidine or prodrugs of fluorinated pyrimidines (such as 5' deoxy-fluorouridine derivatives like Tegafur (5-fluoro-1-(tetrahydro-2-furfuryl)uracil), 5'-deoxyfluorouridine, or related derivatives), acyl derivatives of non-methylated pyrimidine nucleosides may be used in several ways. In one embodiment of the invention, the acyl derivative of a non-methylated pyrimidine nucleoside is administered several hours to one day after a dose of a fluorouracil prodrug such as Tegafur, similar to the situation with parenteral administration of fluorouracil described above. In this context, the delayed administration of the acyl derivative of a non-methylated pyrimidine nucleoside results in reduced toxicity of the fluorinated pyrimidine toward normal tissues. In another embodiment of the invention, the acyl derivative of a non-methylated pyrimidine nucleoside is administered at the same time as, or within about an hour of, the orally-active antineoplastic agent.

Tegafur, an orally active 5-fluorouracil prodrug, is currently administered clinically in a formulation containing uracil in a molar ratio of four parts uracil to one part tegafur. In this context, uracil potentiates the antitumor efficacy of 5-fluorouracil produced by degradation of tegafur (during and after absorption from the intestinal tract into the bloodstream) by competing with 5-fluorouracil for the enzyme which breaks down both pyrimidine molecules, dihydropyrimidine dehydrogenase. However, uracil also potentiates the toxicity of 5-fluorouracil toward normal tissues, particularly the intestine. Gastrointestinal damage is the primary dose-limiting toxicity of a mixture of tegafur and uracil. Co-administration of Tegafur (or other orally active antineoplastic pyrimidine analogs) with an acyl derivative of a non-methylated pyrimidine nucleoside results in the desirable potentiation of the syste is toxicity of, for example, 5-fluorouracil derived from Tegafur, without potentiating its toxicity toward the intestinal mucosa as drastically as does uracil itself. The acyl derivative of a non-methylated pyrimidine nucleoside and the orally active antineoplastic nucleoside analog are administered in ways and at dosages and molar ratios typically used for administration of uracil and an orally active antineoplastic agent. See, for example, U.S. Pat. No. 4,328, 229, hereby incorporated by reference. Higher doses of the orally active antineoplastic agent are also possible with the use of the acyl derivatives of the subject invention. This embodiment of the invention is experimentally demonstrated in Examples 13 and 14 below.

Acyl derivatives of deoxycytidine are advantageous in treating or preventing toxicity due to antineoplastic nucleoside analogs that are specifcally analogs of cytidine, e.g. arabinosyl cytosine or prodrugs thereof, cyclocytidine, 5-aza-2'-deoxycytidine, arabinosyl 5-azacytosine, or 6-azacytidine. For oral administration, advantageous acyl derivatives of deoxycytidine are those substituted with short-chain fatty acids, especially acetate.

In a typical clinical situation involving the use of arabinosyl cytosine or related antineoplastic analogs of cytidine, which are primarily utilized for treatment of leukemias, the acyl derivative(s) of deoxycytidine are administered orally, in a dose of 0.5 to 10 grams, either before or after administration of a dose of Ara-C is completed, or concurrently with the dose of Ara-C. Further doses of the acyl derivative of deoxycytidine are administered every six to eight hours for 1 to 4 days. Repetitions of this treatment regimen are initiated once per week or less frequently, depending on the clinical response.

It is intended that the antineoplastic agents be used for treating the types of tumors for which they are normally utilized, e.g. Ara-C and its related cytidine analogs are effective in leukemias, fluorouracil and related fluorinated uridine analogs are useful in treating tumors of the colon, stomach, pancreas, and head-and-neck. In one embodiment, the antineolastic agents are administered in their normal doses, in which case the compounds of the invention primarily reduce the severity of toxic side effects. In another embodiment, the antineoplastic agents are administered in doses higher than normal, in which case the compounds of the invention permit safer administration of such higher, therapeutically aggressive doses of the anticancer drugs. Furthermore, the increases in therapeutic index of anticancer agents resulting from use of the compounds and compositions of the invention permit the use of particular antineoplastic agents for treating tumors for which they are not currently standard therapy.

Treatment of Complications Associated with Viral Infection

HIV-infected patients, especially those whose infection has progressed to "acquired immunodeficiency syndrome" (AIDS), suffer from a variety of symptoms and diseases which result from and, in some cases, further exacerbate a severely compromised immune system. Many of these patients are given antiviral chemotherapeutic agents, such as AZT, which also have detrimental effects on the body's immune function and upon hematopoiesis, further lowering resistance to infections of all kinds. Administration of the compounds of the invention—orally, intravenously, or by parenteral injection—raises the low blood cell counts due to antiviral chemotherapy agents, particularly those that modify nucleotide synthesis, metabolism, or utilization, such as AZT or dideoxycytidine. Because anemia and greater susceptibility to infections are dose- and rate-limiting factors in chemotherapeutic treatment of AIDS patients, treatment of the patients with these compounds reduces chemotherapeutic side effects (and thus improves the quality of life) and, if appropriate, permits a more intensive chemotherapeutic regimen to be employed. AZT and dideoxycytidine produce deleterious side effects in tissues other than bone marrow, including muscle and the peripheral nervous system. The compounds and compositions of the invention are also useful for treating or preventing such side effects.

Various antiviral nucleoside analogs other than AZT and dideoxycytidine are used to treat viral infections, including but not limited to HIV, herpes, or hepatitis. Examples of such agents include 5-ethyl-2'-deoxyuridine, 5-iodo-2'-deoxyuridine, 5-bromo-2'-deoxyuridine, 5-methylamino-2'-deoxyuridine, 2',3'-dideoxycytidin-2'-ene, 3'-deoxythymidin-2'-ene, 3'-azido-2',3'-dideoxyuridine, arabinosyluracil, dideoxyuridine, 2',3'-dideoxy-3'-fluorothymidine and (S)-1-(3-hydroxy-2-phosphonylmethoxypropyl)cytosine (HPMPC); see also WO 89/09603, hereby incorporated by reference. The compounds of the invention are used to treat or prevent deleterious side effects of these and related other antiviral nucleoside analogs.

In treatment or prevention of toxicity due to antiviral chemotherapy, the compounds and compositions are administered prior to, during and/or after administration of the antiviral agents. Typical antiviral chemotherapy regimens, especially for chronic viral infections such as HIV infection, involve daily (often multiple daily) administration of the antiviral agent or agents. The compounds of the invention are administered, several times daily, daily, or less frequently, depending on the clinical effect observed. In all cases, the antiviral drugs are typically administered in their normal regimens for the types of viral infections for which they are clinically useful. Treatment of patients receiving antiviral nucleoside analogs is undertaken either to reduce side effects of a standard dose or to permit administration of doses of antiviral agents higher than are normally tolerated or utilized.

For treatment of toxicity due to AZT, acyl derivatives of either or both uridine, cytidine, or deoxycytidine are useful. Particularly advantageous are acyl derivatives of deoxycytidine. For oral administration, acyl derivatives of deoxycytidine, uridine, and cytidine substituted with short chain fatty acids (particularly acetate) or with short chain carbyloxycarbonates (e.g. ethoxycarbonate), are advantageous.

In a typical clinical situation, a patient receives AZT two to four times daily, and must generally do so indefinitely. Doses of 1 to 10 grams of acyl derivatives of uridine, cytidine, or deoxycytidine (or mixtures of two or all three) are administered orally once per week up to about four times per day, depending on the clinical response.

For treatment or prevention of toxicity due to dideoxycytidine, acyl derivatives of deoxycytidine are advantageous.

Treatment of Complications Associated with Malarial Infection

Malarial parasites, e.g. *Plasmodium yoelii* or *Plasmodium falciparum*, are dependent upon de novo synthesis pathways for pyrimidine nucleotide biosynthesis; mammalian cells in general can utilize either de novo pathways or "salvage" pathways, through which advanced nucleotide precursors such as uridine or cytidine are incorporated into intracellular nucleotide pools.

5-Fluoroorotate, an analog of the pyrimidine nucleotide precursor orotic acid, is toxic toward malarial parasites which are dependent on de novo pyrimidine biosynthesis. Other inhibitors of de novo pyrimidine biosynthesis, such as PALA, pyrazofurin or 6-azauridine are also similarly toxic toward malaria parasites. Inhibitors of pyrimidine biosynthesis, including especially fluoroorotate, are also toxic toward mammals. However, administration of uridine to mammals treated with 5-fluoroorotate (or other inhibitors of pyrimidine biosynthesis) attenuates host toxicity due to the latter without impairing its antimalarial activity. Orally active agents which elevate blood uridine levels are advantageous sources of uridine in this context. Such agents include the acyl derivatives of uridine or cytidine of the invention. In treatment of malaria, an effective anti-malarial dose of fluoroorotate is administered. Before, after, or at the same time as fluoroorotate administration, an acyl derivative of uridine or cytidine (triacetyluridine is particularly advantageous) is administered, in a dose sufficient to attenuate fluoroorotate toxicity. Typical doses of an acylated uridine or cytidine derivative such as triacetyl uridine range from 1 to 10 grams, administered as often as needed to minimized fluoroorotate toxicity, e.g. one to four times per day. Doses of fluoroorotate or uridine are optionally repeated as necessary to overcome the malarial infection and to reduce host toxicity respectively.

E. ADMINISTRATION AND FORMULATION OF COMPOUNDS AND COMPOSITIONS OF THE INVENTION

The compounds and compositions of the invention are administered orally, by parenteral injection, intravenously, topically, or by other means, depending on the condition being treated.

The optimal doses and dose schedules for triacetyluridine (or other acyl derivatives of uridine, cytidine, deoxycytidine or deoxyuridine) are readily determined by one skilled in the art, by monitoring the therapeutic effect.

The compounds and compositions of the invention are administered chronically or intermittently. The compounds and compositions are administered prior to, during, or after an exposure to cytoreductive or antiviral chemotherapy agents, depending on the characteristics of the toxicity of the chemotherapy agents.

Advantageous acyl derivatives of uridine, cytidine, deoxycytidine, or deoxyuridine for oral administration are those substituted with short chain (2-6 carbon) fatty acids on the hydroxyl groups of their ribose or deoxyribose rings. Also advantageous for oral administration are pyrimidine nucleosides substituted on their hydroxyl groups with hydrocarbyloxycarbonyl radicals containing 3-7 carbon atoms.

Dosages for orally administered acyl derivatives of uridine, cytidine, deoxycytidine or deoxyuridine typically range from 0.5 to 20 grams per day, most commonly 2 to 10 grams per day.

Powdered acyl derivatives of uridine, cytidine, deoxycytidine or deoxyuridine are administered orally in capsule or tablet form, although solutions, emulsions, or suspensions are also useful for oral administration.

The compounds of the invention are optionally formulated in biodegradable, bioerodible, or other gradual-release matrices for sustained release of the compounds after oral administration or subcutaneous implantation. In the case of intravenous or intramuscular injection, the compounds are optionally formulated in liposomes.

The pharmacologically active compounds optionally are combined with suitable pharmaceutically acceptable carriers comprising excipients and auxiliaries which facilitate processing of the active compounds. These are administered as tablets, dragees, capsules, and suppositories. The compositions are administered, for example, orally, rectally, vaginally, or released through the buccal pouch of the mouth, and are optionally applied in solution form by injection, orally or by topical administration. The compositions may contain from about 0.1 to 99 percent, preferably from about 50 to 90 percent, of the active compound(s), together with the excipient(s).

For parenteral administration by injection or intravenous infusion, the active compounds are suspended or dissolved in aqueous medium such as sterile water or saline solution. Injectable solutions or suspensions optionally contain a surfactant agent such as polyoxyethylenesorbitan esters, sorbitan esters, polyoxyethylene ethers, or solubilizing agents like propylene glycol or ethanol. The solution typically contains 0.01 to 5% of the active compounds. The active compounds optionally are dissolved in pharmaceutical grade vegetable oil for intramuscular injection. Such preparations contain about 1% to 50% of the active compound(s) in oil.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose and/or polyvinyl pyrrolidone.

Auxiliaries include flow-regulating agents and lubricants, for example, silica, talc, stearic acid or salts thereof, such as magnesium stearate or calcium stearate and/or polyethylene glycol. Dragee cores are provided with suitable coatings which, if desired, are resistant to gastric juices. For this purpose, concentrated sugar solutions are used, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dyestuffs or pigments are optionally added to the tablets or dragee coatings, for example, for identification or in order to characterize different compound doses.

The pharmaceutical preparations of the present invention are manufactured in a manner which is itself known, for example, by means of conventional mixing, granulating, dragee-making, dissolving, or lyophilizing processes. Thus, pharmaceutical preparations for oral use are obtained by combining the active compound(s) with solid excipients, optionally grinding the resulting mixture and processing the mixture of granules, after adding suitable auxiliaries, if desired or necessary, to obtain tablets or dragee cores.

Other pharmaceutical preparations which are useful for oral delivery include push-fit capsules made of gelatin, as well as soft-sealed capsules made of gelatin and a plasticizer such as glycerol or sorbitol. The push-fit capsules contain the active compound(s) in the form of granules which optionally are mixed with fillers such as lactose, binders such as starches and/or lubricants such as talc or magnesium stearate, and, optionally stabilizers. In soft capsules, the active compounds are preferably dissolved or suspended in suitable liquids such as fatty oils, liquid paraffin, or polyethylene glycols. In addition, stabilizers optionally are added.

Suitable formulations for parenteral administration include aqueous solutions of the active compounds in water soluble form, for example, water soluble salts. In addition, suspensions of the active compounds as appropriate in oily injection suspensions are administered. Suitable lipophilic solvents or vehicles include fatty oils, for example, sesame oil, or synthetic fatty acid esters, for example, ethyl oleate or tri-glycerides. Aqueous injection suspensions optionally include substances which increase the viscosity of the suspension which include, for example, sodium carboxymethylcellulose, sorbitol and/or dextran. The suspension optionally contains stabilizers.

In another embodiment, the active compounds are formulated as part of a skin lotion for topical administration. Suitable lipophilic solvents or vehicles include fatty oils, for example sesame oil or coconut oil, or synthetic fatty acid esters, for example ethyl oleate or triglycerides.

In another embodiment, the active compounds are formulated in vehicles suitable for direct treatment of gastrointestinal mucosa. Examples include mouthwashes, liquids (solutions or suspensions) to be swallowed, or viscous fluids (e.g. solutions of methylcellulose, carboxymethylcellulose, xanthan gum, etc.) which are administered orally or rectally.

Other pharmaceutical preparations which are used rectally, especially for treatment of the colon and rectum, include, for example, suppositories which consist of a combination of active compounds with a suppository base. Suitable suppository bases are, for example, natural or synthetic triglycerides, paraffin hydrocarbons, polyethylene glycols or higher alkanols. In addition, gelatin rectal capsules which consist of a combination of the active compounds with a base are useful. Base materials include, for example, liquid triglycerides, polyethylene glycols, or paraffin hydrocarbons.

F. SYNTHESIS OF THE COMPOUNDS OF THE INVENTION

Acylated derivatives of non-methylated pyrimidine nucleosides are synthesized by reacting a pyrimidine nucleoside with an activated carboxylic acid. An activated carboxylic acid is one that has been treated with appropriate reagents to render its carboxylate carbon more susceptible to nucleophilic attack than is the case in the original carboxylic acid. Examples of useful activated carboxylic acids for synthesis of the compounds of the invention are acid chlorides, acid anhydrides, n-hydroxysuccinimide esters, or carboxylic acids activated with BOP-DC. Carboxylic acids are alternatively linked to pyrimidine nucleosides with coupling reagents like dicyclohexylcarbodiimide (DCC).

During preparation of the acyl compounds of the invention, when the acid source of the desired acyl derivative has groups which interfere with the acylation reactions, e.g., hydroxyl or amino groups, these groups are blocked with protecting groups, e.g., t-butyldimethylsilyl ethers or t-BOC groups, respectively, before preparation of the anhydride. For example, lactic acid is converted to 2-t-butyldimethyl-siloxypropionic acid with t-butyl-dimethylchlorosilane, followed by hydrolysis of the resulting silyl ester with aqueous base. The anhydride is formed by reacting the protected acid with DCC. With amino acids, the N-t-BOC or N-CBZ derivative is prepared, using standard techniques, which is then converted to the anhydride with DCC. With acids containing more than one carboxylate group (e.g., succinic, fumaric, or adipic acid) the acid anhydride of the desired dicarboxylic acid is reacted with a pyrimidine nucleoside in pyridine or pyridine plus dimethylformamide or dimethylacetamide.

Amino acids are coupled to the exocyclic amino groups of cytosine and deoxycytosine, and to hydroxyl groups on the aldose moiety of pyrimidine nucleosides, by standard methods using DCC in a suitable solvent, particularly a mixture of (i) methylene chloride and (ii) dimethylacetamide or dimethylformamide.

Carbyloxycarbonyl derivatives of non-methylated pyrimidine nucleosides are prepared by reacting the nucleoside with the appropriate carbylchloroformate in a solvent such as pyridine or pyridine plus dimethylformamide under anhydrous conditions. The solvent is removed under vacuum, and the residue is purified by column chromatography.

It will be obvious to the person skilled in the art that other methods of synthesis may be used to prepare the compounds of the invention.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLES

Example 1

Oral Administration of Triacetyluridine Ameliorates Hematologic Toxicity of 5-Fluorouracil Purpose This study was undertaken in order to determine if oral administration of TAU could rescue mice from 5-FU toxicity more effectively than oral administration of uridine itself. Bone marrow cellularity and peripheral blood cell counts were used as an index of 5-FU toxicity.

Methods

Forty-five female Balb/C mice (20 grams each) were given 5-fluorouracil (150 mg/kg, i.p.) at 12:00 noon on the initial day of the experiment. These animals were then divided into 5 groups: control (water, p.o.), oral uridine at 400 mg/kg/dose, oral uridine at 800 mg/kg/dose, parenteral (i.p.) uridine at 400 mg/kg/dose, and oral TAU at 500 mg/kg/dose.

Two hours after administration of 5-FU, the rescue treatments with uridine or triacetyluridine were begun. Groups received their designated treatment at 2:00 p.m., 4:00 p.m., and 6:00 p.m. on the day of 5-FU administration, and at 9 a.m., 11:00 a.m., 1:00 p.m., 3:00 p.m. and 5:00 p.m. on the following day. Each dose of uridine or TAU was administered in 0.2 ml of water by gavage or in 0.2 ml of saline by i.p. injection, as appropriate.

Seven days after administration of 5-FU, blood (0.2-0.3 ml) from five mice in each group was collected from the suborbital sinus into EDTA for subsequent differential blood cell counting. Mice were sacrificed by cervical dislocation; femurs were removed, and their cell contents were expelled for counting; spleens were also removed and weighed. Thirteen days after administration of 5-FU, the remaining four mice in each group were bled, sacrificed, and their spleens removed.

Results

Day Seven

5-FU administration resulted in declines in counts of all blood cell types examined. Seven days after administration of 5-FU, neutrophil, lymphocyte, and platelet counts in animals treated with oral TAU were significantly higher than in control animals (Table 1). It is particularly noteworthy that leukocyte counts in the mice that received TAU were higher than in mice that received an equimolar dose of uridine by intraperitoneal injection. Cell counts in the mice that received oral TAU were also higher than in mice that received uridine orally at either equimolar (400 mg/kg/dose) or twice equimolar doses (800 mg/kg/dose).

Platelet counts were within the normal range (700-800 K/µl) in the mice that received oral TAU and i.p. uridine. They were subnormal in the other groups, and lowest in the control mice (Table 1).

Bone marrow cell counts were significantly greater in the mice treated with TAU orally and with uridine parenterally than any of the other groups (Table 2)

Day Eleven

Importantly, neutrophil and RBC levels were higher in the group that received TAU than in the other treatment groups, including mice that received an equimolar dose of uridine by intraperitoneal injection (Table 3).

Spleen weight is an index of hematopoietic activity in mice recovering from bone marrow damage. Eleven days after 5-FU, spleen weight was significantly higher in mice given oral TAU compared to the other treatment groups; spleens were smallest in the control group (Table 4).

Conclusion

The results of this study show that oral administration of TAU rescues mice from 5-FU toxicity more effectively than oral administration of equimolar and twice equimolar uridine itself, and more effectively than an equimolar dose of uridine given by intraperitoneal injection.

TABLE 1

Blood cell counts 7 days after 5-FU

| | WBC | Neutrophils | Lympho-cytes | Platelets | RBC |
|---|---|---|---|---|---|
| Control | 3.4 ± .1 | 0.24 ± .05 | 3.18 ± .07 | 387 ± 72 K/µl | 8.05 ± .11 |
| Urd 400 oral | 4.4 ± .5* | 0.48 ± .23 | 3.01 ± .77 | 434 ± 114 | 7.66 ± .12 |
| Urd 800 oral | 4.6 ± .4* | 0.88 ± .22* | 3.76 ± .27 | 646 ± 108 | 8.24 ± .26 |
| Urd 400 i.p. | 4.6 ± .4* | 0.83 ± .24* | 3.80 ± .30 | 773 ± 54** | 8.06 ± .05 |
| TAU 500 oral | 5.9 ± .4* | 1.20 ± .23** | 4.72 ± .36** | 723 ± 57** | 8.27 ± .16 |

All blood cell count units are K/µl except RBC's, which are M/µl
* = greater than control value, P < .05
** = greater than control value, P < .01

TABLE 2

Marrow cell counts and spleen weight 7 days after 5-FU

| | Marrow cell counts | Spleen weight |
|---|---|---|
| Control | 1.5 ± .2 × 10$^6$/femur | 71 ± 2.6 mg |
| Urd 400 oral | 1.6 ± .2 × 10$^6$ | 74 ± 2.4 |
| Urd 800 oral | 2.9 ± .9 × 10$^6$ | 74 ± 6.4 |
| Urd 400 i.p. | 5.0 ± .7 × 10$^{6}$** | 78 ± 5.5 |
| TAU 500 oral | 3.0 ± .5 × 10$^{6}$* | 78 ± 3.5 |

* = greater than control value, P < .05
** = greater than control value, P < .01

TABLE 3

Blood cell counts 11 days after 5-FU

| | WBC | Neutrophils | Lympho-cytes | Platelets | RBC |
|---|---|---|---|---|---|
| Control | 5.2 ± .3 | 0.48 ± .12 | 4.68 ± .11 | 2280 ± 193 | 7.31 ± .05 |
| Urd 400 oral | 4.6 ± .5 | 0.84 ± .19 | 3.65 ± .27 | 1940 ± 177 | 7.44 ± .14 |
| Urd 800 oral | 4.9 ± .4 | 0.82 ± .19 | 4.07 ± .38 | 2127 ± 143 | 7.33 ± .16 |
| Urd 400 i.p. | 5.1 ± .5 | 1.20 ± .21* | 3.84 ± .38 | 1706 ± 88 | 7.78 ± .22 |
| TAU 500 oral | 5.4 ± .5 | 1.89 ± .12** | 3.29 ± .36 | 1446 ± 160 | 8.05 ± .16** |

All blood cell count units are K/µl except RBC's, which are M/µl
* = greater than control value, P < .05
** = greater than control value, P < .01

TABLE 4

Spleen weight 11 days after 5-FU

| | Spleen weight |
|---|---|
| Control | 76 ± 7 mg |
| Urd 400 oral | 103 ± 15 |
| Urd 800 oral | 99 ± 6* |
| Urd 400 i.p. | 104 ± 6* |
| TAU 500 oral | 143 ± 11** |

* = greater than control value, P < .05
** = greater than control value, P < .01

Example 2

TAU Accelerates Hematopoietic Recovery in 5-FU-Treated Animals in a Dose Dependent Manner Purpose The purpose of this experiment was to confirm and extend the previous findings that orally administered TAU accelerates hematopoietic recovery in mice treated with 5-fluorouracil (5-FU), and to observe the relationship between increasing doses of TAU and the responses of the hematopoietic system of these 5-FU-treated mice.

Methods

Seventy female Balb/C mice weighing approximately twenty grams were each given an i.p. injection of 5-FU (150 mg/kg) at 1:00 p.m. on the initial day of the study. These animals were then divided into five different treatment groups: control (water), and oral TAU at doses of 100, 250, 500, and 1,000 mg/kg/treatment. The test compounds were then given at 3:00, 5:00, 7:30, and 10:00 p.m. on the day of 5-FU administration; at 9:00 a.m., 11:00 a.m., and 1:00, 3:00, 6:00, and 10:00 p.m. the following day; and a final administration at 11:00 a.m. two days following the single 5-FU injection. Each treatment was given orally in a volume of 0.2 ml water (by gavage), except the highest dose of TAU which was administered in 0.4 ml of water.

On days seven and eleven following 5-FU administration, blood (0.2-0.3 ml) was collected from seven mice in each group by retro-orbital bleeding into EDTA for subsequent differential blood cell counting. Mice were sacrificed by cervical dislocation; their right femurs removed and the contents expelled for cell counting; and their spleens removed and weighed.

Results

Day Seven.

With increasing doses of TAU there were increasing numbers of nucleated cells in the bone marrow. While the number of such cells in the group receiving TAU 100 was approximately equal to that in the control group, differences in bone marrow cellularity were significantly greater in the TAU 500 and TAU 1,000 groups compared that of controls (Table 5).

Treatment with TAU at doses of 500 and 1,000 mg/kg/treatment resulted in white blood cell counts significantly greater than those in the control group.

Total neutrophil counts also appeared to increase in a dose-dependent manner, reaching approximately three-fold higher levels in the TAU 1,000 group compared to controls.

In both the TAU 500 and TAU 1,000 groups lymphocyte counts were significantly elevated compared to those in the control group.

Platelet counts were significantly elevated in the TAU 250, 500, and 1,000 groups. The dose-response curve appeared to plateau at about 500 mg/kg/treatment (Table 6).

TABLE 5

Effect of increasing doses of TAU on hematopoiesis in mice seven days after 5-FU administration. All blood cell counts are K/μl.

| | Marrow | WBC | Neut | Lym |
|---|---|---|---|---|
| Control | 1.70 ± .35 | 2.46 ± .13 | .026 ± .011 | 2.43 ± .13 |
| TAU 100 | 1.77 ± .18 | 2.47 ± .04 | .014 ± .008 | 2.46 ± .04 |
| TAU 250 | 2.91 ± .48 | 2.76 ± .20 | .027 ± .012 | 2.71 ± .20 |

TABLE 5-continued

Effect of increasing doses of TAU on hematopoiesis in mice seven days after 5-FU administration. All blood cell counts are K/μl.

| | Marrow | WBC | Neut | Lym |
|---|---|---|---|---|
| TAU 500 | 3.93 ± .39* | 4.06 ± .14* | .037 ± .020 | 3.99 ± .15* |
| TAU 1000 | 4.42 ± .34* | 3.57 ± .25* | .071 ± .027 | 3.44 ± .23* |

*indicates different from control, p < .01

TABLE 6

Effect of increasing doses of TAU on red blood cells (RBC) and platelets (PLT) in mice seven days after 5-FU administration.

| | RBC (M/μl) | PLT (K/μl) |
|---|---|---|
| Control | 8.38 ± .18 | 308 ± 52 |
| TAU 100 | 8.20 ± .07 | 440 ± 46 |
| TAU 250 | 8.51 ± .06 | 601 ± 46** |
| TAU 500 | 8.43 ± .16 | 712 ± 42** |
| TAU 1000 | 8.65 ± .15 | 715 ± 35** |

**indicates different from control, p < .01

Day Eleven.

Spleen weight was somewhat elevated at every dose of TAU compared to controls, but reached statistical significance only in the TAU 250 group (104.2±3.5 mg versus 79.7±3.1; p<0.05)

Total neutrophil counts were significantly greater than control values in the TAU 250, 500, and 1,000 groups.

Red blood cell counts were significantly increased in the TAU 500 group (8.72±0.18×$10^6$ per microliter) and the TAU 1000 group (8.63±0.16×$10^6$ per microliter) compared to controls (7.90±0.09×$10^6$ per microliter). The hematocrit followed a similar pattern (Table 7).

TABLE 7

Effect of increasing doses of TAU on hematocrit (HCT) in mice seven (7 d) and eleven (11 d) days after 5-FU administration.

| | Control | T100 | T250 | T500 | T1000 |
|---|---|---|---|---|---|
| HCT (7 d) | 38.50 ± .88 | 37.77 ± .37 | 40.04 ± .38 | 39.50 ± .61 | 40.84 ± .68 |
| HCT (11 d) | 36.94 ± 0.51 | 36.80 ± .88 | 37.47 ± .83 | 41.16 ± .88 p < .01 | 41.55 ± .77 p < .001 |

Conclusions

The results of this experiment confirm and extend the previous findings that treatment of animals receiving the chemotherapeutic agent 5-FU with TAU dramatically reverses the detrimental effects of 5-FU on the hematopoietic system, and that it does so in a dose-dependent manner.

Example 3

Acyl Derivatives of Uridine Ameliorate Bone Marrow Toxicity of 5-Fluorouracil Purpose The purpose of this experiment was to test and compare the efficacy of uridine and derivatives of uridine in attenuating damage to the hematopoietic system of mice caused by the chemotherapeutic agent 5-fluorouracil (5-FU).

Methods

Ninety-eight female Balb/C mice weighing approximately 20 grams each were given a one-time 150 mg/kg injection (i.p.) of 5-FU at 1 p.m. on the initial day of the study. These animals were then divided into seven groups: control (saline), uridine (300 mg/kg/treatment), triacetyluridine (TAU; 455 mg/kg/treatment), benzoyluridine (BU; 428 mg/kg/treatment), ethoxycarbonyl (ECU; 389 mg/kg/treatment), octanoyluridine (OU; 455 mg/kg/treatment), and valeryluridine (VU; 403 mg/kg/treatment). All of these doses are equimolar, and were administered in a volume of 0.4 ml by i.p. injection. The groups were treated at 3:30, 6:00, and 8:30 p.m. on the initial day with their respective agents. On the following day these compounds were administered at 9:30 a.m., 12:00 noon, 2:30, and 5:00 p.m. One final treatment was given on the next day at 10:00 a.m.

On days seven and eleven following 5-FU administration, blood (0.2-0.3 ml) was collected from seven mice in each group by retro-orbital bleeding into EDTA for subsequent differential blood cell counting. Mice were sacrificed by cervical dislocation; their right femurs removed and the contents expelled for cell counting; and their spleens removed and weighed.

Results

Day Seven.

Even at this first time point each of the uridine derivatives accelerated one or more aspects of hematopoietic recovery following 5-FU damage. Thus, spleen weight was elevated in all of the groups compared to saline controls. These differences reached statistical significance ($p<0.05$) in the uridine ($80.4\pm7.8$ mg), ECU ($75.7\pm5.0$ mg), and VU ($69.1\pm1.7$ mg) groups when compared to controls ($62.7\pm1.8$).

TAU increased bone marrow cellularity by 40% over control values ($4.50\pm0.77\times10^3$ per microliter versus $2.78\pm0.45\times10^3$ per microliter, respectively).

White blood cell counts were significantly elevated in both the ECU-treated ($7.26\pm0.31\times10^3$ per microliter; $p<0.01$) and VU-treated ($6.57\pm0.49\times10^3$ per microliter; $p<0.05$). groups compared to saline controls ($4.60\pm0.70\times10^3$ per microliter).

Platelet counts were significantly greater in the groups treated with uridine ($785.3\pm57.5\times10^3$ per microliter; $p<0.02$), BU ($829.6\pm\times10^3$ per microliter; $p<0.01$), and VU ($825.7\pm26.7\times10^3$ per microliter; $p<0.002$) than those in the saline-treated controls ($523.2\pm71.4\times10^3$ per microliter).

There was a trend toward higher total neutrophil counts in nearly all of the treatment groups, but only VU ($0.141\pm0.027\times10^3$ per microliter) was actually statistically significantly greater ($p<0.002$) than saline controls ($0.013\pm0.009\times10^3$ per microliter).

Lymphocyte counts were significantly greater in the groups treated with ECU ($7.19\pm0.32\times10^3$ per microliter; $p<0.01$) and VU ($6.42\pm0.49\times10^3$ per microliter) than in the saline-treated controls ($4.59\pm0.70\times10^3$ per microliter).

At the doses used in this particular experiment, octanoyluridine, having the longest carbon chain of any of the other derivatives, proved to be somewhat detrimental. There were not enough animals from this group to provide day 11 data. However, in dose optimization studies (see Example 3A), octanoyluridine administered at a lower dose showed very beneficial effects on hematopoietic recovery following 5-FU.

Day Eleven.

Virtually every index of hematopoietic function, including spleen weight, white blood cell counts, red blood cell counts, hematocrit, neutrophil counts, and lymphocyte count, was significantly improved by treatment with the uridine derivatives used in this experiment (Table 8). Spleen weights were elevated above those of controls ($94.7\pm7.4$) in each treatment group, reaching statistical significance ($p<0.05$) in the uridine ($121.6\pm9.7$), BU ($126.9\pm12.3$), and VU ($139.4\pm8.0$) groups.

Conclusions

A wide variety of the uridine derivatives of the invention are effective in ameliorating damage caused by administration of the chemotherapeutic agent 5-FU.

TABLE 8

Effect of uridine and derivatives of uridine on hematopoiesis in mice eleven days after 5-FU administration. White blood cell counts (WBC), neutrophil counts (Neut), and lymphocyte counts (lym) are all expressed in K/µl; red blood cell counts (RBC) in M/µl.

|  | WRC | RBC | HCT % | Neut | Lym |
|---|---|---|---|---|---|
| Con | 3.37 ± .68 | 7.11 ± .1 | 32.97 ± 0.4 | .09 ± .047 | 3.3 ± .7 |
| Urd | 5.20 ± .47* | 7.32 ± .2 | 34.67 ± 0.9 | .60 ± .180** | 4.6 ± .4 |
| TAU | 6.23 ± .55** | 7.35 ± .2 | 35.01 ± 1.2 | .55 ± .164** | 5.6 ± .4* |
| BU | 6.20 ± .49** | 7.62 ± .1** | 36.87 ± 0.6** | 1.04 ± .295** | 5.1 ± .4* |
| ECU | 5.51 ± .64* | 7.65 ± .2* | 37.54 ± 1.0** | .66 ± .166** | 4.8 ± .5* |
| VU | 6.31 ± .42** | 7.83 ± .1** | 38.31 ± 0.8** | .97 ± .136** | 5.2 ± .4* |

*indicates different from Control, $p < .05$
**indicates different form Control, $p < .01$
Con = control; Urd = uridine; TAU = triacetyluridine; BU = benzoyluridine; ECU = ethoxycarbonyluridine; VU = valeryluridine Con=control; Urd=uridine; TAU=triacetyluridine;

BU=benzoyluridine;

ECU=ethoxycarbonyluridine; VU=valeryluridine

Example 3A

Octanoyl Uridine Attenuates Hematological Toxicity of 5-FU

Purpose

The purpose of this experiment was to test the efficacy of octanoyluridine (Oct-U) in ameliorating the toxic effects of 5-fluorouracil (5-FU) on hematopoiesis.

Methods

Fourteen Balb/C female mice weighing approximately 20 grams each were given a one-time 75 mg/kg i.p. injection of 5-FU at 11:00 a.m. on the initial day of the study. Half of these animals were subsequently treated with Oct-U (100 mg/kg/treatment, i.p.), while the other half (controls) were injected with physiological saline. Administration of Oct-U and saline occurred at 2:30, 4:30, and 7:00 p.m. on the initial day, and at 9:30 a.m., 12:00 noon, 2:30, and 5:00 p.m the following day. An additional group of seven mice (basals) received no 5-FU and no treatments.

Results

Administration of 5-FU resulted in statistically significant damage to the hematopoietic system as measured by each and every index employed in this study, including spleen weight, bone marrow cellularity, WBC-count, total neutrophil count, lymphocyte counts, RBC count, hematocrit percent, and platelet count (Tables 9 and 10). Subsequent treatment of mice receiving 5-FU with Oct-U resulted in substantial improvement in each and all of these parameters of hematopoietic function (Table 9 and 10).

Conclusion

Treatment of mice receiving 5-FU with octanoyl uridine ameliorates the toxic effects of 5-FU on hematopoiesis.

TABLE 9

Effect of octanoyluridine on bone marrow cellularity and myelopoiesis in mice seven days after 5-FU administration. All counts are in thousands per microliter.

| | Marrow | WBC | Neut | Lym |
|---|---|---|---|---|
| Basal | 8.96 ± .32 | 6.89 ± .25 | 1.85 ± .24 | 4.78 ± .23 |
| Control | 4.16 ± .40* | 4.04 ± .19* | 0.26 ± .03* | 3.74 ± .19* |
| Oct-U | 7.73 ± .68** | 5.96 ± .47** | 1.19 ± .22** | 4.62 ± .29** |

*indicates $p < .01$ versus basals
**indicates $p < .01$ versus controls

TABLE 10

Effect of octanoyluridine on red blood cells (RBC), platelets (PLT), and spleen weight in mice seven days after 5-FU administration.

| | RBC (M/μl) | PLT (K/μ) | Spleen weight (mg) |
|---|---|---|---|
| Basal | 8.56 ± .17 | 897 ± 21 | 83.6 ± 1.7 |
| Control | 7.98 ± .13* | 963 ± 13* | 75.4 ± 2.4* |
| Oct-U | 8.13 ± .14 | 1243 ± 59** | 87.2 ± 3.7** |

*indicates $p < .05$ versus basal
**indicates $p < .05$ versus control

Example 4

Plasma Uridine Levels after Administration of Acyl Derivatives of Uridine

Methods

Plasma uridine levels were determined in mice at various times (15 minutes, 30 minutes, 1 hour, and 2 hours) after administration of the acyl derivatives of uridine utilized in Example 3 for attenuation of toxicity caused by 5-FU. Groups of mice (n=3 per compound per time point) received intraperitoneal injections of uridine (300 mg/kg), triacetyluridine (TAU; 455 mg/kg/treatment), benzoyluridine (BU; 428 mg/kg/treatment), ethoxycarbonyluridine (ECU; 389 mg/kg/treatment), octanoyluridine (OU; 455 mg/kg/treatment), and valeryluridine (VU; 403 mg/kg/treatment). The doses of the acyl derivatives of uridine are the molar equivalent of 300 mg/kg uridine. At the appropriate time points, blood samples (200 μl) were taken from mice via the retro-orbital sinus and immediately centrifuged. 75 μl of the resulting plasma was deproteinized with 2 volumes of methanol followed by centrifugation. The supernatant was lyophilized and reconstituted with 50 mM potassium phosphate buffer, pH 6.0, and analyzed for uridine content by HPLC on a reverse phase ($C_{18}$) column. Uridine was separated from other plasma components in 50 mM potassium phosphate buffer, pH 6.0, with a methanol gradient (2% to 35% over 15 minutes). Uridine was detected and quantified by UV absorbance at 260 nM.

Results

Administration of all of the acyl derivatives of uridine tested resulted in increased plasma uridine levels, as shown in Table 11. Plasma uridine levels in control animals (mice that received no exogenous uridine or cytidine derivatives) were 1.1±0.1 μM.

TABLE 11

Plasma uridine concentration in mice after administration of acyl derivatives of uridine

| | Time: | | | |
|---|---|---|---|---|
| | 15 min | 30 min | 1 hr | 2 hr |
| Compound: | Plasma Uridine Concentration (μM) | | | |
| Uridine | 911 ± 35 | 415 ± 86 | 185 ± 21 | 5.3 ± 1.5 |
| Triacetyluridine | 666 ± 70 | 348 ± 28 | 24.5 ± 7.5 | 15.1 ± 1.6 |
| Benzoyluridine | 1160 ± 45 | 353 ± 87 | 178 ± 54 | 8.6 ± 1.7 |
| Valeryluridine | 1001 ± 113 | 347 ± 117 | 266 ± 1.41 | 7.4 ± 0.4 |
| Octanoyluridine | 56 ± 22 | 14 ± 7.4 | 17 ± 2.9 | 2.2 ± 0.04 |
| Ethoxycarbonyluridine | 250 ± 18 | 83 ± 0.1 | 44 ± 12 | 2.0 ± 1.6 |

Administration of all of the acyl derivatives of uridine results in elevated plasma uridine levels. The acyl derivatives provide sustained formation of uridine via gradual deacylation. This may not be reflected in plasma uridine levels, since cellular uptake of uridine can remove uridine from the circulation as it is formed by deacylation of the acylated uridine derivatives. It is important to note that the acylated uridine derivatives are generally superior to an equimolar quantity of uridine in attenuating toxicity due to 5-FU (Table 8 in Example 3)

Example 5

Improved Therapeutic Index of 5-FU (I): TAU Rescue with 5-FU Alone in Tumor-Bearing Mice Purpose The purpose of this experiment was to assess and compare the ability of uridine and TAU to increase the therapeutic index of 5-FU in a tumor-bearing mouse model.

Methods

Sixty CD8F1 (BALB/C×DBA/8) female mice with first generation transplants of CD8F1 spontaneous mammary adenocarcinoma were treated with a weekly chemotherapy regimen which included a single dose of 5-FU (150 mg/kg) followed by various rescue strategies. The average tumor size was 157 mg at the start of the chemotherapy. The weekly chemotherapy course was completed three times.

In order to evaluate the various rescue therapies, the animals were divided into six groups of ten animals each as follows:

| 1. | Saline: | Saline (no 5-FU) |
| 2. | 5-FU alone: | 5-FU (150 mg/kg i.p.) |
| 3. | 5-FU + vehicle: | 5-FU (150 mg/kg i.p.) + vehicle[1] |
| 4. | 5-FU + i.p. uridine: | 5-FU (150 mg/kg i.p.) + Uridine (3,500 mg/kg i.p.) |
| 5. | 5-FU + oral uridine: | 5-FU (150 mg/kg i.p.) + Uridine (5,000 mg/kg p.o.)[2] |
| 6. | 5-FU + oral TAU: | 5-FU (150 mg/kg i.p.) + TAU (7,582 mg/kg p.o.)[2] |

[1] 1:1 oil-water emulsion + 2.5% Tween/BO
[2] 7,582 mg TAU and 5,000 mg uridine are molar equivalent doses.

Results

At the conclusion of three weeks of chemotherapy, mortality in each group was compared and, where a sufficient number of animals survived, body weight and tumor size were compared. The results are summarized as follows in Table 12:

TABLE 12

Effect of combined administration of 5-FU and TAU or uridine

| Group | Mortality | Average Final Tumor Weight (mg) |
| --- | --- | --- |
| 1. Saline | 3/10 | 7,391 |
| 2. 5-FU alone | 9/10 | * |
| 3. 5-FU + vehicle | 10/10 | * |
| 4. 5-FU + i.p. uridine | 1/10 | 1,604 |
| 5. 5-FU + oral uridine | 0/10 | 896 |
| 6. 5-FU + oral TAU | 1/10 | 1,013 |

*Not meaningful due to high mortality.

Mortality in the group receiving only saline was due to the progress of the disease, whereas mortality among the groups receiving 5-FU but no rescue was due to the toxicity of 5-FU itself.

Conclusion

TAU and uridine are effective in rescuing tumor-bearing mice from the toxic effects of 5-FU. Both agents increase the therapeutic index of 5-FU in tumor-bearing mice, and allow higher doses of the drug to be tolerated, with a commensurate increase in anti-cancer effect.

Example 6

Improved Therapeutic Index of 5-FU (II): TAU Rescue with Combination Chemotherapy in Tumor-Bearing Mice Purpose The purpose of this experiment was to assess and compare the ability of TAU and uridine to increase the therapeutic index of 5-FU when used in combination with Phosphonacetyl-L-aspartate (PALA), methotrexate (MTX), and leucovorin (LV), in a drug dosing regimen which increases the cytotoxic potential of 5-FU.

Methods

Forty male CD8F1 mice with transplanted CD8F1 spontaneous breast tumors (initial tumor weight of 155 mg) were treated weekly with the following regimen:

| PALA--19 hr--> | MTX--2.5 hr--> | 5-FU--2 hr--> | LV--19 hr--> | LV |
| --- | --- | --- | --- | --- |
| 100 mg/kg | 300 mg/kg | 150 mg/kg | 300 mg/kg | 300 mg/kg |

In order to evaluate and compare the efficacy of TAU and uridine, the mice were divided into four groups of ten animals each.

| 1. Control: | Saline |
| --- | --- |
| 2. Uridine i.p.: | Uridine (3,500 mg/kg) |
| 3. Uridine (oral): | Uridine (4,000 mg/kg) |
| 4. TAU (oral): | TAU (6,066 mg/kg[1]) |

[1]Molar equivalent of 4000 mg/kg uridine.

Saline, uridine, or TAU was administered every eight hours for a total of 5 treatments starting two hours after each weekly dose of 5-FU. This weekly regimen was repeated for three successive weeks. One week after the third course of chemotherapy regimen, mortality in each group was assessed and, where a sufficient number of animals survived, body weight and tumor weight were also measured.

Results

TABLE 13

Effect of TAU on mortality of tumor-bearing mice receiving combined chemotherapy

| Group | Mortality | Average Final Tumor Weight (mg) |
| --- | --- | --- |
| Control | 10/10 | ** |
| Uridine i.p. | 0/10 | 110 |
| Uridine p.o. | 5/10 | ** |
| TAU p.o. | 1/10 | 162 |

**Not meaningful due to high mortality.

Mortality in the control group was due to toxicity of 5-FU. The tumor weight in untreated mice at this time point averages approximately 3000 milligrams.

Conclusion

TAU and uridine improve the therapeutic index of 5-FU used in this clinically, relevant combination of agents. Oral TAU was as effective as intraperitoneally-administered uridine and more effective than an equimolar dose of orally-administered uridine.

Example 7

Oral Administration of Diacetyldeoxycytidine Attenuates Hematopoietic Toxicity of Arabinosyl Cytosine Purpose The purpose of this experiment was to test the efficacy of diacetyldeoxycytidine (DAdC) and palmitoyldeoxycytidine (PdC) in ameliorating the toxic effects of the chemotherapeutic agent arabinosylcytosine (Ara-C) on the hematopoietic system.

Methods

Twenty-one Balb/C female mice weighing approximately 20 grams each received a daily intraperitoneal injection of Ara-C (100 mg/kg) for five days. These mice were divided into three treatment groups: oral administration of water (controls); oral administration of DAdC (411 mg/kg/treatment); and intraperitoneal administration of PdC (200 mg/kg/treatment in 0.2% Tween 80). Mice were treated with either water, DAdC, or PdC twice daily, at 9 a.m. and 6 p.m. Treatment volume in each case was 0.2 ml. An additional seven mice received no Ara-C and no treatment at all (basals).

On days seven and eleven following 5-FU administration, blood (0.2-0.3 ml) was collected from the seven mice in each group by retro-orbital bleeding into EDTA for subsequent differential blood cell counting. Mice were sacrificed by cervical dislocation, and their spleens removed and weighed.

Results

Ara-C administration resulted in significantly depressed spleen weights, WBC counts, total neutrophil counts, lymphocyte counts, and platelet counts in the control mice compared to the basal mice (Table 14). No toxic effects of Ara-C were observed on erythropoiesis per se (RBC counts, hemoglobin, and hematocrit).

Treatment of mice with DAdC orally and treatment with PdC intraperitoneally significantly reversed the detrimental effects of Ara-C on hematopoiesis. Spleen weight, WBC counts, total neutrophil counts, and platelet counts were all significantly greater than those in control mice (Table 14).

Conclusions

Administration of DAdC or PdC to mice receiving Ara-C ameliorates the toxic effects of Ara-C on the hematopoietic system.

TABLE 14

The effect of diacetyldeoxycytidine (DAdC) or palmitoyldeoxycytidine (PdC) treatment on hematopoiesis in mice receiving arabinosylcytosine (Ara-C) for five days. Spleen weight is in milligrams, WBC, neutrophil, and platelet counts are expressed as K/μl.

|  | Spleen | WBC | Neut | PLT |
| --- | --- | --- | --- | --- |
| Basal | 93.0 ± 2.5 | 8.66 ± .53 | 1.84 ± .12 | 854 ± 30 |
| Control | 37.1 ± 1.3 | 3.60 ± .55 | 0.04 ± .02 | 230 ± 21 |
| DAdC | 87.8 ± 3.5** | 5.00 ± .42 | 0.42 ± .05** | 728 ± 64** |
| PdC | 126.0 ± 5.3** | 5.20 ± .35* | 1.22 ± .27** | 327 ± 30* |

*indicates p < .05 versus control
**indicates p < .001 versus control

Example 8

Orally Administered TAU Ameliorates the Detrimental Effects on the Hematopoietic System of the Antiviral Chemotherapeutic Agent Azidothymidine (AZT) in Drinking Water Purpose The purpose of this experiment was to test the efficacy of orally administered triacetyluridine (TAU) in attenuating the hematopoietic damage caused by the antiviral chemotherapeutic agent azidothymidine (AZT).

Methods

Forty-two Balb/C female mice, each weighing approximately 19 grams, were divided into three different groups of 14 animals each. The three groups were: basal (no AZT, no treatment), control (AZT, water), and TAU (AZT, TAU at 460 mg/kg/treatment). AZT was administered ad libitum in the drinking water at a concentration of 1.5 mg/ml throughout the course of the experiment. The volume of AZT solution consumed in all treatment groups was similar and averaged 2.25 ml per day per mouse, resulting in a daily AZT dose of about 170 mg/kg per day. Water and TAU were administered in a volume of 0.2 mL three times per day for the first 24 days of the study, and twice each day thereafter.

All of the animals were weighed on the day the experiment began, once each week, and immediately prior to sacrifice. After weighing the mice on days 24 and 35, blood (0.2-0.3 ml) was collected from seven mice in each group by retroorbital bleeding into EDTA for subsequent differential blood cell counting, including reticulocytes. Mice were then sacrificed by cervical dislocation; their right femurs removed and the contents expelled for cell counting; and their spleens removed and weighed.

Results

Body weights of the mice receiving AZT alone were significantly reduced (17.55±0.47 grams, p<0.002) compared to those of basal animals (19.78±0.38) at day 7, while the body weights of mice treated with TAU (19.51±0.38) were nearly identical to those of basals and significantly greater (p<0.005) than those of controls at this same time point. This trend was also observed on day 13, although there were no statistically significant differences between groups. Again on day 24 of this experiment, the body weights of the AZT controls were statistically depressed compared to both basals (p<0.001) and TAU-treated mice (p<0.05). At this time point the body weights of the TAU-treated animals were also less than those of basal animals.

Day 24

The RBC counts of the mice receiving AZT only (8.49±0.16) were significantly reduced (p<0.01) compared to basals (9.07±0.11). The RBC counts of those animals treated with TAU (9.01±0.09) were not significantly different from basals and were significantly greater (p<0.02) than those of controls.

Total neutrophil counts were also significantly reduced (p<0.02) in the mice receiving only AZT (0.67±0.09) compared to basals (1.02±0.08). Neutrophil levels in those animals treated with TAU (0.91±0.06) were not significantly different from basals, and were significantly greater (p<0.05) than those in the AZT-only group.

Day 35

Significant detrimental effects of AZT were seen with virtually every parameter employed at this time point. Bone marrow cellularity, WBC counts, and lymphocyte counts were significantly depressed as were RBC counts, hemoglobin, hematocrit compared to those from basal mice (Table 15). Mean cell volume, mean cell hematocrit, and platelet counts of the control mice were significantly elevated compared to those of the basal mice (Table 14). All of these parameters indicate AZT-induced hematopoietic damage.

Treatment with oral TAU resulted in significantly higher RBC counts, hemoglobin, and hematocrit compared to AZT controls (Table 15), as well as significantly lower mean cell volume, mean cell hematocrit, and platelet counts compared to the control values (Table 16).

While reticulocyte number was significantly elevated in the control group (0.256×10$^6$ per microliter; p<0.001) versus basal counts (0.129×10$^6$ per microliter), those mice treated with TAU had reticulocyte levels significantly higher (0.371× 10$^6$ per microliter) than both basals (p<0.001) and controls (p<0.01).

Conclusions

From these data it is clear that orally administered TAU has beneficial effects in animals with AZT-induced hematopoietic damage.

TABLE 15

TAU ameliorates the detrimental effects of AZT on erythropoiesis in mice. Red blood cell (RBC) counts are in M/μl, hematocrit (HCT) is expressed as a percentage, and hemoglobin (HGB) is gm/dl.

|  | RBC | HCT | HGB |
| --- | --- | --- | --- |
| Basal | 9.04 ± .08 | 42.52 ± .34 | 15.57 ± .09 |
| Control | 7.53 ± .13 | 39.29 ± .59 | 14.57 ± .26 |
| TAU | 8.20 ± .20** | 41.26 ± .62* | 15.14 ± .12* |

*indicates p < .05 versus control
**indicates p < .01 versus control

TABLE 16

TAU attenuates AZT-induced cell damage. Platelet counts (PLT) are in K/µl, mean cell volume (MCV) is in fl, and mean cell hematocrit (MCH) is measured in picograms.

|  | PLT | MCV | MCH |
|---|---|---|---|
| Basal | 736 ± 24 | 47.03 ± .16 | 17.23 ± .13 |
| Control | 903 ± 18 | 52.16 ± .37 | 19.37 ± .20 |
| TAU | 809 ± 06** | 50.41 ± .48* | 18.49 ± .28* |

*indicates $p < .05$ versus control
**indicates $p < .01$ versus control

Example 9

Orally Administered TAU Ameliorates the Detrimental Effects on the Hematopoietic System of Intraperitoneally Administered AZT Purpose The purpose of this experiment was to test the efficacy of orally administered TAU in reversing the hematopoietic damage caused by parenteral administration of azidothymidine (AZT).

Methods

AZT (100 mg/kg i.p.) was given three times daily at 9 a.m., 4 p.m., and at 10 p.m. to fifty-six female Balb/C mice weighing approximately 19 grams each. Three times each day, at 9 a.m., 4 p.m., and 10 p.m., animals were treated with either water (control) or TAU at doses of 230, 460, or 920 mg/kg/treatment by oral intubation. Treatment volume was 0.2 ml for the control and TAU 460 groups, 0.1 ml for the TAU 230 group, and 0.4 ml for the TAU 920 group. One additional group of fourteen mice was not given AZT or any treatments (basal).

All of the animals were weighed on the day the experiment began, on day six and on day 13. After weighing the mice on days six and thirteen blood (0.2-0.3 ml) was collected from seven mice in each group by retro-orbital bleeding into EDTA for subsequent differential blood cell counting, including reticulocytes. Mice were then sacrificed by cervical dislocation; their right femurs removed and the contents expelled for cell counting; and their spleens removed and weighed.

Results

Day Six.

Bone marrow cellularity was significantly greater ($p<0.05$) in the group treated with the 230 mg/kg TAU (8.89±0.46) than in the group receiving AZT alone (7.54±0.23).

White blood cell counts were $8.23±0.38×10^3$ per microliter in the basal group. AZT reduced the WBC count to $6.8±0.66×10^3$ per microliter, but when mice were treated with TAU (920 mg/kg) in addition to receiving AZT, WBC counts were restored to basal levels ($8.46±0.63×10^3$ per microliter).

AZT administration resulted in a drop in RBC levels from $9.14±0.10×10^6$ per microliter (basals) to $8.80±0.31×10^6$ per microliter (controls). No such decrement was seen in mice receiving TAU (460 mg/kg/treatment) and AZT ($9.15±0.07×10^6$ per microliter).

Day Thirteen.

For virtually every parameter employed in this study those mice given AZT alone for 13 days showed statistically significant evidence of hematopoietic damage. Thus, WBC counts, RBC counts, hemoglobin, hematocrit, reticulocyte counts, total neutrophil counts, and lymphocyte counts were all significantly depressed, while mean cell hematocrit and platelet counts were significantly elevated. Concomitant treatment of mice receiving AZT with TAU (460 mg/kg/treatment) resulted in statistically significant improvement in each and all of these measures (Table 17 and 18).

Conclusions

Concomitant treatment of mice with AZT and TAU significantly improves hematopoietic function. This is true for both the white blood cell and red blood cell indices.

TABLE 17

Oral TAU attenuates AZT-induced damage to the myelopoietic system in mice. These data were obtained on day 13 of the study.

|  | WBC K/µl | Neutro. K/µl | Lymph. K/µl | Platelets K/µl |
|---|---|---|---|---|
| Basal | 6.8 ± 0.6 | 127 ± 0.11 | 5.14 ± 0.33 | 680 ± 30 |
| Control | 5.1* ± 0.28 | 0.49* ± 0.07 | 4.02* ± 0.27 | 1025* ± 44 |
| TAU | 7.0** ± 0.37 | 0.62 ± 0.03 | 6.06** ± 0.38 | 863** ± 26 |

*= different from Basal group, $P < .05$
**= different from Control group, $P < .05$

TABLE 18

Oral TAU attenuates AZT-induced damage to the erythropoietic system in mice. These data were obtained on day 13 of the study.

|  | RBC M/µl | HGB G/dL | HCT % | Retic. M/µl |
|---|---|---|---|---|
| Basal | 9.16 ± 0.06 | 15.32 ± 0.18 | 43.18 ± 0.54 | 0.298 ± 0.028 |
| Control | 8.15* ± 0.07 | 14.08* ± 0.13 | 38.90* ± 0.43 | 0.086* ± 0.007 |
| TAU | 8.58** ± 0.08 | 14.54** ± 0.13 | 40.83** ± 0.37 | 0.162** ± 0.014 |

*= different from Basal group, $P < .05$
**= different from Control group, $P < .05$

Example 10

Oral Administration of Diacetyldeoxycytidine (DAdC) Ameliorates Hematopoietic Toxicity Produced by Intraperitoneally Administered AZT in DBA Mice Purpose The purpose of this experiment was to test the efficacy of orally administered DAdC in reversing the hematopoietic damage caused by parenteral administration of the antiviral chemotherapeutic agent azidothymidine (AZT).

Methods

AZT (100 mg/kg i.p.) was given three times daily at 9 a.m., 4 p.m., and at 10 p.m. to twenty-eight female DBA mice weighing approximately 20 grams each. Three times each day, at 9 a.m., 4 p.m., and 10 p.m., animals were treated with either water (control) or DAdC (411 mg/kg/treatment) by oral intubation. Treatment volume was 0.2 ml. One additional group of fourteen mice was not given AZT or any treatment (basal).

During the first few days of treatment a total of eight mice died from accidents occurring during oral administration of the water and DAdC. Therefore, the number of animals in the control group and the DAdC group were reduced on the days of sacrifice as follows: On day 6 there were four mice in the control group and five in the DAdC group; on day 13 there were seven in the control group and three in the DAdC group. The number of basal animals was seven at both time points.

On days six and thirteen blood (0.2-0.3 ml) was collected from mice in each group by retro-orbital bleeding into EDTA for subsequent differential blood cell counting, including reticulocytes. The animals were then sacrificed by cervical dislocation; their right femurs removed and the contents expelled for cell counting; and their spleens removed and weighed.

Results

Day Six

By day 6 AZT administration resulted in statistically significant hematopoietic damage, especially in those mice not receiving DAdC (controls). Thus, WBC and lymphocyte counts were significantly depressed in the controls compared to the basals, as were RBC counts, hemoglobin (HGB), hematocrit (HCT), and reticulocyte counts (Table 17). Platelet counts were significantly elevated in these control mice. Bone marrow cell counts were also reduced 23% in the control group compared to the basals.

In contrast, those mice receiving AZT but also treated with DAdC had only a slight (2.5%) reduction in bone marrow cellularity and were not statistically different from basals. RBC counts, HGB, HCT, and reticulocyte counts in the DAdC group were not different from those in the basal group, but were significantly greater than those in the control group (Table 19).

Day Thirteen

Mice given AZT alone for 13 days showed statistically significant evidence of hematopoietic damage in nearly every category compared to basal animals. Concomitant treatment of mice with DAdC markedly attenuated or reversed the AZT-induced erythropoietic damage (Table 20) as was seen on day 6. Platelet counts were also significantly improved in mice treated with DAdC (769±32; p<0.02) compared to control animals (950±34).

Conclusions

Treatment of mice receiving AZT with DAdC significantly improves hematopoietic function, especially erythropoiesis.

TABLE 19

The effect of diacetyldeoxycytidine (DAdC) treatment on erythropoiesis in mice receiving AZT for six days.

| | RBC | HGB | HCT | Reticulocytes |
|---|---|---|---|---|
| Basal | 9.47 ± .18 | 13.93 ± .20 | 40.83 ± 0.83 | .326 ± .039 |
| Control | 8.53 ± .33* | 12.60 ± .40* | 36.32 ± 1.54* | .017 ± .004* |
| DAdC | 9.49 ± .32** | 13.96 ± .40** | 40.84 ± 1.35** | .205 ± .075** |

*indicates different from Basal, $p < .05$
**indicates different from Control $p < .05$

TABLE 20

The effect of diacetyldeoxycytidine (DAdC) treatment on erythropoiesis in mice receiving AZT for thirteen days.

| | RBC | HGB | HCT | Reticulocytes |
|---|---|---|---|---|
| Basal | 9.95 ± .13 | 14.83 ± .19 | 42.83 ± 0.41 | .637 ± .044 |
| Control | 8.51 ± .05* | 13.06 ± .07* | 37.21 ± 0.13* | .365 ± .022* |
| DAdC | 9.16 ± .32** | 13.97 ± .39** | 41.53 ± 1.17** | .814 ± .069** |

*indicates different from Basal, $p < .05$
**indicates different from Control, $p < .05$ Example 11

Orally Administered Diacetyldeoxycytidine (DAdC) or Tetrahydrouridine (THU) Ameliorate the Detrimental Effects on the Hematopoietic System of Intraperitoneally Administered AZT in Balb/C Mice Purpose The purpose of this experiment was to test the efficacy of orally administered DAdC or parenterally administered THU in reversing the hematopoietic damage caused by parenteral administration of the antiviral chemotherapeutic agent azidothymidine (AZT).

Methods

AZT (100 mg/kg i.p.) was given three times daily at 9 a.m., 4 p.m., and 10 p.m. to twenty-one female Balb/C mice weighing approximately 20 grams each. Three times each day, at 9 a.m., 4 p.m., and 10 p.m., seven animals were treated with either water (control, p.o.) or DAdC (300 mg/kg/treatment, p.o.), or THU (12.5 mg/kg/treatment in 0.2% Tween 80, i.p.). Treatment volume was 0.2 ml. One group of seven mice was not given AZT or any treatment (basal).

On day thirteen blood (0.2-0.3 ml) was collected from mice in each group by retro-orbital bleeding into EDTA for subsequent differential blood cell counting, including reticulocytes. The animals were then sacrificed by cervical dislocation; their right femurs removed and the contents expelled for cell counting; and their spleens removed and weighed.

Results

Concomitant treatment of mice with DAdC markedly attenuated or reversed AZT-induced erythropoietic damage (Table 21). Total neutrophil counts were also significantly improved in mice treated with DAdC (1.39±0.14; p<0.01) compared to control animals (0.74±0.10).

Mice given AZT and receiving THU treatment showed significant improvements in myelopoiesis compared to controls as well as erythropoiesis. Total white blood cell counts were significantly greater in the THU group (6.06±0.35; p<0.05) than in the control group (4.73±0.36). Significant differences (p<0.05) were also observed comparing the total neutrophils counts in the THU-treated group (1.16±0.15) with those of the controls (0.74±0.10). Lymphocyte counts were improved, but the differences did not reach statistical significance in this experiment. In addition, reticulocyte indices (percent and M/μl) were significantly greater (p<0.05) in the THU-treated group compared to those in the control group.

Conclusions

Treatment of Balb/C mice receiving AZT with DAdC or THU significantly improves hematopoietic function.

TABLE 21

The effect of diacetyldeoxycytidine (DAdC) treatment on erythropoiesis in Balb/C mice receiving AZT for thirteen days.

| | RBC | HGB | HCT | Retic |
|---|---|---|---|---|
| Basal | 8.63 ± .11 | 15.37 ± .08 | 41.01 ± 0.52 | .089 ± .009 |
| Control | 7.55 ± .11* | 13.71 ± .22* | 35.96 ± 0.46* | .039 ± .004* |
| DAdC | 8.26 ± .13** | 14.97 ± .15** | 39.51 ± 0.61** | .059 ± .006** |

*indicates different from Basal, $p < .05$
**indicates different from Control, $p < .05$

Example 12

Plasma Uridine Levels after Oral Administration of Uridine or Triacetyluridine (TAU), with or without Dipyridamole Purpose The purpose of this experiment was to demonstrate that TAU is a more effective orally-active agent for elevating plasma uridine levels than is uridine itself, and furthermore to demonstrate the effect of dipyridamole (DPM), a nucleoside uptake-blocker which also has antiviral activity, on plasma uridine levels after administration of TAU or uridine.

Methods

Female Balb/C mice with a body weight of 20 grams were divided into four groups of 8 animals each:

1. Uridine (1000 mg/kg) p.o.

2. TAU (1500 mg/kg) p.o.

3. Uridine (1000 mg/kg) p.o.+DPM (25 mg/kg i.p.)

4. TAU (1500 mg/kg) p.o.+DPM (25 mg/kg i.p.)

(1500 mg/kg TAU is the molar equivalent of 1000 mg/kg uridine)

Dipyridamole was administered by intraperitoneal injection 30 minutes prior to uridine or TAU Uridine was administered orally by gavage as an aqueous solution in a volume of 0.4 ml.

TAU was administered by gavage in an emulsion vehicle (1:1 corn oil/water with 2.5% Tween 80).

Two mice from each group were bled from the suborbital plexus at each time point: 0 (Basal uridine levels before TAU or uridine administration), 0.5, 1, 2, and 4 hours after administration of TAU or uridine Plasma samples (0.1 ml) were deproteinized by addition of 0.2 ml methanol followed by centrifugation. Samples were lyophilized and then reconstituted with HPLC buffer (100 mM ammonium acetate, pH 6.5, for subsequent assay of uridine by reverse phase HPLC with UV absorbance detection (254 nm).

Data points are the mean of two samples for each time point.

Results

After oral administration of uridine, plasma uridine reached peak concentrations of 6 micromolar. In contrast, oral administration of an equimolar dose of TAU resulted in peak plasma uridine levels of 260 micromolar, thus demonstrating the marked advantage of TAU over uridine as an orally active means of elevating plasma uridine levels.

Dipyridamole further enhanced (approximately two-fold) the amplitude (peak uridine levels of 460 micromolar) and duration of blood uridine levels after oral administration of TAU.

Dipyridamole similarly improved blood uridine level maintenance after oral uridine, although levels were much lower than in the corresponding mice that received TAU (peak plasma uridine levels of 20 micromolar).

These results are summarized in Table 22.

TABLE 22

Plasma uridine concentrations after oral administration of uridine or TAU, with or without dipyridamole.
Plasma uridine levels (μM) after TAU or uridine administration

| Treatment | 0 hr | 0.5 hr | 1 hr | 2 hr | 4 hr |
|---|---|---|---|---|---|
| Uridine | 2 | 4 | 6 | 4 | 2 |
| TAU | 2 | 240 | 260 | 110 | 12 |
| Uridine + DPM | 2 | 10 | 20 | 10 | 4 |
| TAU + DPM | 2 | 280 | 460 | 440 | 32 |

Conclusions

Plasma uridine levels after oral administration of TAU were much higher than were observed after oral administration of uridine. TAU is thus a much better source of plasma uridine after oral administration than is uridine itself. Dipyridamole inhibits uridine uptake into some cell types, and thereby enhances the amplitude and duration of plasma uridine concentrations after administration of TAU or uridine.

Example 13

Modulation of Toxicity of Oral Tegafur with TAU and Uracil

Purpose:

Tegafur (5-fluoro-1-(tetrahydro-2-furfuryl)uracil) is an orally active prodrug of 5-fluorouracil; it is enzymatically converted to 5-FU during and after absorption from the intestinal tract into the bloodstream. For treatment of cancer, Tegafur, is typically administered orally in a formulation also containing uracil, in a 1:4 molar ratio of Tegafur to uracil; tegafur formulated with uracil is currently used clinically in humans. Uracil potentiates the activity of the 5-FU formed from Tegafur by competitively inhibiting dihydrouracil dehydrogenase, an enzyme which degrades 5-FU.

After administration of high doses of tegafur+uracil, mice lose a substantial amount of body weight, indicating gastrointestinal toxicity. After oral administration, it is believed that uracil potentiates the local toxicity of 5-FU formed in intestinal cells during passage of Tegafur into the bloodstream. It is therefore desirable to utilize with tegafur, or other orally active prodrugs of 5-FU, an agent which inhibits breakdown of 5-FU (or otherwise potentiates its activity) primarily in the circulation (after absorption) rather than locally in the gut.

Triacetyluridine (TAU), like other acyl derivatives of uridine and cytidine of the invention, is converted to uridine and uracil during and after absorption into the bloodstream; when present at the same time as 5-FU, both uridine and uracil are capable of potentiating 5-FU cytotoxicity. Therefore, the cytotoxicity of oral Tegafur+uracil versus Tegafur+TAU was assessed. Blood cell counts were utilized as an index of cytotoxicity of 5-FU in the circulation (and by extension, of antitumor potency). Body weight loss was used as an index of gastrointestinal toxicity.

Methods:

Three groups of mice received Tegafur by oral intubation in a dose of 400 mg/kg per mouse. The initial body weight of mice in each group was 19.0±0.6 grams. One of these groups also received uracil in a molar ratio of 4:1 to the tegafur dose, and another group received TAU, also in a 4:1 molar ratio to Tegafur. Body weights were monitored. Six days after Tegafur administration, blood samples were taken for differential cell counts.

Results:

Tegafur alone at a dose of 400 mg/kg produced a significant drop in neutrophil numbers, but did not significantly affect platelet counts; body weight was reduced only slightly (7%) compared to untreated (basal) animals. Tegafur plus uracil produced a more severe drop in neutrophil counts than did Tegafer alone, and also reduced platelet counts and caused a substantial (29%) loss of body weight. Tegafur plus TAU produced blood cell count changes similar to those found after tegafur plus uracil, but did not cause a change in body weight. The blood cell counts found after oral administration of either Tegafur+TAU or Tegafur+uracil are similar to those observed after a therapeutically effective dose of 5-fluorouracil (e.g. 150 mg/kg) administered systemically. However, the weight loss caused by Tegafur+uracil is unacceptable in the context of cancer chemotherapy. The excellent systemic cytotoxicity of oral Tegafur+TAU (better than Tegafur alone and at least equivalent to Tegafur+uracil) and the absence of a loss in body weight (especially in contrast to the marked weight loss in animals receiving Tegafur+TAU) indicate that TAU is useful in potentiating systemic cytotoxicity (and therefore antitumor potency) of orally-active fluorouracil prodrugs without a proportional increase in gastrointestinal toxicity. Combination of an orally active fluorouracil prodrug with an acylated non-methylated pyrimidine nucleoside derivative therefore permits better oral delivery of therapeutically effective amounts of the important antineoplastic drug fluorouracil than is obtained with current methods and compositions.

TABLE 23

Uracil vs TAU for enhancing cytotoxicity of Tegafur

|  | Body weight (grams) | Neutrophils (K/μl) | Platelets (K/μl) |
|---|---|---|---|
| Basal | 19.6 ± 0.5 | 2.60 ± 0.510 | 984 ± 25 |
| Tegafur-400 | 18.2 ± 0.7 | 0.40 ± 0.085* | 956 ± 30 |
| Tegafur-400 + Uracil | 14.0 ± 0.3* | 0.02 ± 0.002* | 448 ± 31* |
| FT-400 + TAU | 19.8 ± 0.4 | 0.02 ± 0.003* | 334 ± 33* |

*Different from Basal values, P < .01

All drugs were administered orally in a single dose. Blood samples were taken for cell counts 6 days after drug administration; body weights were also recorded at this time.

Example 14

Antitumor Efficacy of Tegafur and TAU vs Tegafur and Uracil

Purpose

Tegafur (FT) is an orally active prodrug of fluorouracil. Uracil, at an optimum molar ratio of 4:1, potentiates the antitumor efficacy of FT. The dose limiting toxicity of the FT-uracil combination is damage to the intestinal mucosa. Increasing doses of FT-uracil also result in hematopoietic damage.

The purpose of the present study was to compare the antitumor efficacy of FT in combination with either uracil or triacetyluridine (TAU) in rats bearing the Walker 256 carcinosarcoma. The essential question addressed in this experiment was whether or not FT+TAU inhibits tumor growth as well as FT+uracil, while causing less intestinal toxicity (body weight changes). Blood cell damage was also assessed and compared.

Methods

Animals

Male Sprague-Dawley rats with an initial body weight of approximately 120 grams.

Tumors

Pooled ascites fluid containing Walker 256 cells at a density of $2.47 \times 10^8$ cells/milliliter was collected from three donor rats. An aliquot containing $4.94 \times 10^7$ cells was injected subcutaneously in the right flank of each rat in the anti-tumor efficacy study. This resulted in formation of solid subcutaneous tumors.

Treatment

FT was administered at doses of 40, 60, and 80 mg/kg/day in a 1:4 molar ratio with either uracil or TAU. The vehicle used was 1% hydroxypropylmethylcellulose. Treatment was initiated (day 1) five days after tumor implantation. Vehicle and vehicle plus drugs were administered orally by gavage each day for seven days (day 1 through 7) in a volume of 1.2 milliliters per 100 grams of body weight. Tumor size was measured in situ on day 8. On day 10 blood samples were obtained and, after sacrifice of the animals, tumor size and weight were determined.

Treatment Groups

1. Vehicle (control)

2. FT 40 mg/kg+uracil

3. FT 60 mg/kg+uracil

4. FT 80 mg/kg+uracil

5. FT 40 mg/kg+TAU

6. FT 60 mg/kg+TAU

7. FT 80 mg/kg+TAU n=7 animals/group

Measurements

Body weights were determined prior to treatment on days 1, 3, 5, and 7. On day 10 the animals were weighed prior to sampling and sacrifice. Body weights are expressed as the percent of body weight change over the course of the experiment.

Tumor size was measured in situ on day 8 and the tumor volume was then calculated using the following formula:

$$\text{length} \times \text{width}^2 / 2$$

Following sacrifice on day 10 the tumor was exposed, the size measured in situ, and the tumor volume calculated using the formula above. The tumor was then removed and the tumor weight determined. Tumor data are also expressed as T/C %. T/C % is:

$$\text{mean tumor size in drug-treated rats} \times 100 \text{ mean tumor size in control rats}$$

Complete blood cell counts with differential were determined using blood samples obtained by cardiac puncture immediately prior to sacrifice on day 10.

Results

The effects of FT+uracil and FT+TAU on tumors and on body weights as assessed on day 8 are summarized in Table 24. The data show that FT+TAU has greater anti-tumor efficacy and preserves body weight better than equivalent doses of FT+uracil at each dose of FT. For example, at the FT 60 dose the tumor volume and T/C percent for the FT-TAU treated group are less than half those of the uracil-treated group. At that same dose level (FT 60) the body weight change is 52.1% in the FT-TAU group compared to 7.8% in the FT-uracil group. Higher doses of FT are more effective in preventing tumor growth than lower doses.

Tumor and body weight data obtained on day 10 are presented in Table 25. Tumor values—T/C percent, tumor volume and tumor weight—are significantly lower and body weight gains significantly greater in the rats treated with FT-TAU than in those treated with FT-uracil.

The hematopoietic effects of FT treatment are recorded in Table 26. Platelet counts are preserved at all FT dose levels in the FT-TAU treated animals, while dropping precipitously at increasing doses of FT in the FT-uracil groups. Total white, blood cell counts and lymphocytes are also maintained better in the FT-TAU groups at the higher, more effective doses of FT. At the FT 40 dose, neutrophil counts are less severely attenuated in the FT-TAU group than in the equivalent FT-uracil group. In fact, at each FT-TAU dose level, neutrophil counts are approximately twice those observed in the corresponding FT-uracil group.

The results of this experiment indicate that the use of oral TAU in combination with FT has significant advantages over the FT-uracil combination. FT-TAU has greater anti-tumor activity than equivalent doses of FT-uracil while causing less intestinal and hematopoietic damage.

TABLE 24

Antitumor effects of FT with uracil or TAU in rats bearing Walker 256 Carcinosarcoma: Day 8

| Group | Tumor volume (mm³ ± SE) | T/C (%) | Body wt. change (%) |
|---|---|---|---|
| Control | 3098 ± 372 | 100.0 | 100.0 |
| FT 40 + Uracil | 1651 ± 135 | 53.3 | 51.0 |
| FT 60 + Uracil | 1051 ± 123 | 30.8 | −1.7 |
| FT 80 + Uracil | 848 ± 124 | 27.4 | −26.0 |
| FT 40 + TAU | 1244 ± 209 | 40.2 | 78.0 |
| FT 60 + TAU | 1006 ± 114 | 32.5 | 52.0 |
| FT 80 + TAU | 557 ± 49 | 18.0 | 23.7 |

FT dose = mg/kg/day for 7 days
FT/Uracil = 1:4 molar ratio
FT/TAU = 1:4 molar ratio

TABLE 25

Antitumor effects of FT with uracil or TAU in rats bearing Walker 256 Carcinosarcoma: Day 10

| Group | Tumor volume (g ± SE) | T/C (%) | Body wt. change (%) |
|---|---|---|---|
| Control | 4.16 ± 0.55 | 100.0 | 100.0 |
| FT 40 + Uracil | 3.62 ± 0.35 | 87.0 | 62.2 |
| FT 60 + Uracil | 2.80 ± 0.28 | 67.3 | 39.0 |
| FT 80 + Uracil | 1.50 ± 0.58 | 36.1 | −7.5 |
| FT 40 + TAU | 2.14 ± 0.31 | 51.4 | 93.2 |
| FT 60 + TAU | 2.18 ± 0.42 | 52.4 | 58.9 |
| FT 80 + TAU | 1.77 ± 0.25 | 42.5 | 30.3 |

FT dose = mg/kg/day for 7 days
FT/Uracil = 1:4 molar ratio
FT/TAU = 1:4 molar ratio

TABLE 26

Blood cell counts after FT + uracil and FT + TAU: Day 10

| | WBC | Neutrophils | Lymphocytes | Platelets |
|---|---|---|---|---|
| Control | 11.8 ± 0.8 | 1.84 ± .24 | 9.9 ± 0.8 | 844 ± 44 |
| FT 40 + Uracil | 9.7 ± 1.8 | 0.68 ± .18 | 8.5 ± 1.5 | 866 ± 117 |
| FT-60 + Uracil | 5.9 ± 1.1 | 0.27 ± .11 | 5.6 ± 1.0 | 602 ± 147 |
| FT 80 + Uracil | 3.6 ± 1.0 | 0.14 ± .12 | 4.3 ± 1.1 | 171 ± 49 |
| FT 40 + TAU | 8.2 ± 0.9 | 0.91 ± .21 | 7.0 ± 0.8 | 913 ± 117 |
| FT 60 + TAU | 5.3 ± 0.9 | 0.27 ± .05 | 5.0 ± 0.9 | 830 ± 83 |
| FT 80 + TAU | 5.6 ± 0.8 | 0.12 ± .07 | 5.4 ± 0.7 | 534 ± 136 |

All blood cell count units are K/μl
FT dose = mg/kg/day for 7 days
FT/Uracil = 1:4 molar ratio
FT/PN401 = 1:4 molar ratio Example 15

Synthesis of Ethoxycarbonyluridine

To an ice cold solution of 0.5 grams (1.76 millimoles) grams of 2',3'-isopropylidene uridine in 10 ml pyridine, 2.64 mmoles (1.5 equivalents) of ethylchloroformate was added dropwise while stirring. The reaction was allowed to warm up to room temperature (25° C.) and stirred overnight (18 hours), at which point TLC (9:1 chloroform/methanol) showed complete conversion of starting material to a single product. The solvent was removed by rotary evaporation under high vacuum, giving a light beige syrup which was carried over into the subsequent deprotection step.

The syrup was dissolved in 15 ml of 50% formic acid and heated at 60-70° C. for two hours, at which point TLC showed quantitative removal of the isopropylidene group. Water and formic acid were removed by evaporation under high vacuum, giving a light beige-pink syrup which was applied to a silica gel column and eluted with 95:5 chloroform/methanol. Fractions containing the product were collected, pooled, and evaporated, giving a faintly pink glassy product.

The foregoing is intended as illustrative of the present invention but not limiting. Numerous variations and modifications may be effected without departing from the true spirit and scope of the invention.

What is claimed is:

1. A method for treating toxicity due to a pyrimidine nucleoside analog in an animal comprising
administering to said animal a pharmaceutically effective amount of an acylated derivative of uridine or cytidine selected from the group consisting of triacetyluridine and ethoxycarbonyluridine or triacetylcytidine,
wherein said pyrimidine nucleoside analog is selected from the group consisting of 5-fluorouracil (5-FU), Tegafur, 5-fluoroorotate, 5'-deoxy-5-fluorouridine, 5-fluorouridine, 2'-deoxy-5-fluorouridine, fluorocytosine, trifluoromethyl-2'-deoxyuridine, arabinosyl cytosine, cyclocytidine, 5-aza-2'-deoxycytidine, arabinosyl 5-azacytosine, 6-azacytidine, N-phosphonoacetyl-L-aspartic acid (PALA), pyrazofurin, 6-azauridine, azaribine, thymidine, 3-deazauridine, AZT, dideoxycytidine, 5-ethyl-2'-deoxyuridine, 5-iodo-2'deoxyuridine, 5-bromo-2'-deoxyuridine, 5-methylamino-2'-deoxyuridine, arabinosyluracil, dideoxyuridine and (S)-1-(3-hydroxy-2-phosphonylmethoxypropyl) cytosine;

and wherein said toxicity is selected from the group consisting of damage to hematopoietic tissue and damage to mucosal tissues.

2. A method as in claim 1 wherein said toxicity is damage to hematopoietic tissue.

3. A method as in claim 1 wherein said toxicity is damage to mucosal tissues.

4. A method as in claim 1 wherein said administering step also includes administering an inhibitor of uridine phosphorylase selected from the group consisting of benzylacyclouridine, benzyloxybenzylacyclo-uridine, aminomethyl-benzylacyclouridine, aminomethyl-benzyloxybenzylacyclouridine, hydroxymethyl-benzylacyclouridine, hydroxymethyl-benzyloxybenzylacyclouridine, 2,2'-anhydro-5-ethyluridine, 5-benzyl barbiturate, 5-benzyloxybenzyl barbiturate, 5-benzyloxybenzyl-1-[(1-hydroxy-2-ethoxy)methyl]barbiturate, 5-benzyloxybenzylacetyl-1-[(1-hydroxy-2-ethoxy)methyl]barbiturate, and 5-methoxybenzylacetylacyclobarbiturate.

5. A method as in claim 1 wherein said acylated derivative is triacetylcytidine, and said administering step also includes administering an inhibitor of cytidine deaminase selected from the group consisting of tetrahydrouridine and tetrahydro-2'-deoxyuridine.

6. A method as in claim 1 wherein said administering step also includes administering an inhibitor of nucleoside transport selected from the group consisting of dipyridamole, probenicid, lidoflazine and nitrobenzylthioino sine.

7. A method as in claim 1 wherein said administering step also includes administering an agent which enhances hematopoiesis selected from the group consisting of IL-1, IL-2, IL-3, IL-4, IL-5, IL-6, IL-7, IL-8, granulocyte colony stimulating factor, granulocyte/macrophage colony stimulating factor, stem cell factor, erythropoietin, glucan, and polyinosine-polycytidine.

8. A method as in claim 1 wherein said administering step also includes administering a compound capable of enhancing the uptake and phosphorylation of nucleosides into cells selected from the group consisting of insulin and insulinogenic carbohydrate.

9. A method as in claim 1, wherein said acylated derivative of uridine is triacetyluridine.

10. A method as in claim 9, wherein said pyrimidine nucleoside analog is 5-fluorouracil (5-FU).

11. A method as in claim 9, wherein said pyrimidine nucleoside analog is AZT and said toxicity is damage to hematopoietic tissue.

* * * * *